(12) United States Patent
Lelievre et al.

(10) Patent No.: US 9,969,964 B2
(45) Date of Patent: May 15, 2018

(54) DISEASE-ON-A-CHIP

(71) Applicant: Purdue Research Foundation, West Lafayette, IN (US)

(72) Inventors: Sophie Andree Lelievre, West Lafayette, IN (US); Pierre-Alexandre Vidi, West Lafayette, IN (US); James Francis Leary, West Lafayette, IN (US); Teimour Maleki-Jafarabadi, Thousand Oaks, CA (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 259 days.

(21) Appl. No.: 14/577,326

(22) Filed: Dec. 19, 2014

(65) Prior Publication Data

US 2015/0177226 A1 Jun. 25, 2015

Related U.S. Application Data

(60) Provisional application No. 61/919,938, filed on Dec. 23, 2013.

(51) Int. Cl.
*C12M 1/00* (2006.01)
*C12M 3/00* (2006.01)
*C12M 1/12* (2006.01)
*C12M 1/32* (2006.01)

(52) U.S. Cl.
CPC ............ *C12M 23/20* (2013.01); *C12M 23/04* (2013.01); *C12M 23/12* (2013.01)

(58) Field of Classification Search
CPC .... B01L 2300/0883; B01L 2300/0877; C12M 25/06; C12M 23/04; C12M 23/20
See application file for complete search history.

(56) References Cited

U.S. PATENT DOCUMENTS

| | | | | |
|---|---|---|---|---|
| 5,935,430 | A * | 8/1999 | Craig | B01L 3/502707 204/451 |
| 2003/0148401 | A1* | 8/2003 | Agrawal | B01J 19/0046 506/9 |
| 2004/0082058 | A1* | 4/2004 | Schleifer | B01L 3/508 435/287.2 |
| 2009/0281250 | A1* | 11/2009 | DeSimone | B01L 3/502707 525/418 |
| 2010/0233799 | A1* | 9/2010 | Takayama | B01L 3/50273 435/305.2 |
| 2012/0213975 | A1* | 8/2012 | Naisby | B01L 3/502707 428/173 |

OTHER PUBLICATIONS

M.G. Grafton, et al., Breast on-a-chip: mimicry of the channeling system of the breast for development of theranostics, Integr. Biol., 2011, 3, 451-459.
P.-A. Vidi, et al., Disease-on-a-chip: mimicry of tumor growth in mammary ducts, The Royal Society of Chemistry 2013, Lab on a Chip, DOI: 10.1039/c3lc50819f.

* cited by examiner

*Primary Examiner* — Nathan A Bowers
(74) *Attorney, Agent, or Firm* — Purdue Research Foundation; Yonghao Hou

(57) ABSTRACT

The invention generally relates to a cell culture system for coculturing non-neoplastic and neoplastic cells on a planar member which more faithfully mimics the in vivo geometry of a lumen or a cavity.

20 Claims, 29 Drawing Sheets

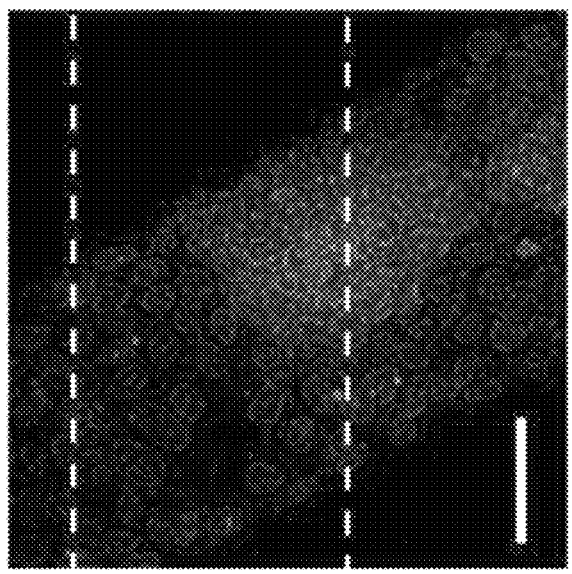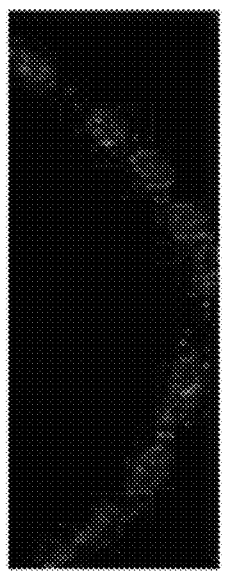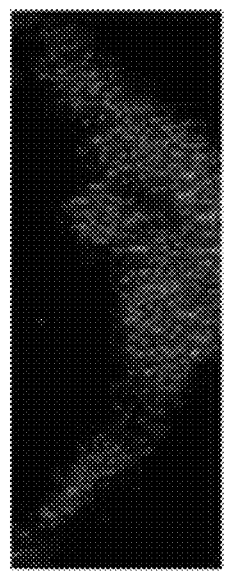
FIG. 19A
FIG. 19B
FIG. 19C

DISEASE-ON-A-CHIP

CROSS-REFERENCE TO RELATED APPLICATIONS

The present U.S. patent application is related to and claims the priority benefit of U.S. Provisional Patent Application Ser. No. 61/919,938, filed Dec. 23, 2013, the contents of which is hereby incorporated by reference in its entirety into this disclosure.

STATEMENT GOVERNMENT INTEREST

This invention was made with government support under W81XWH-09-1-0354 award by the Congressionally-Directed Materials Research Command/Breast Cancer Research Program, and CA163957 awarded by the National Institutes of Health. The government has certain rights in the invention.

TECHNICAL FIELD

This disclosure relates to cell culture apparatus and methods, and in particular to high throughput apparatus that mimic in vivo epithelial cell cultures and tumors.

BACKGROUND

This section introduces aspects that may help facilitate a better understanding of the disclosure. Accordingly, these statements are to be read in this light and are not to be understood as admissions about what is or is not prior art.

Reproducing human pathologies in a tissue context in vitro is paramount for the development of strategies to specifically identify and treat diseased cells amidst a complex organ system. Organs-on-chips that recapitulate tissue architectures have a large potential for theranostic developments. In the breast, glandular units (acini) are grouped into lobules and connected via a branched ductal system to the nipple. The vast majority of breast cancers arise from the inner layer of luminal epithelial cells in the terminal mammary ducts connected to the lobules. Coculture systems combining various cell types have been implemented to engineer normal organs, for instance by layering different cell types and matrices to produce arteries, bladders and portions of liver among other organs or systems. Cocultures of non-neoplastic epithelial and cancer cells have also been reported, but the majority of these models used cell monolayers lacking epithelial tissue architecture or culture inserts preventing direct contact between cancer and non-cancer cells. Few systems allowing contacts between healthy and diseased epithelia have been described, notably to evaluate the influence of non-neoplastic cells on treatment responses by tumor cells, but these systems do not recreate the physiological architecture of the normal tissue. There remains a need for a cell culture system that faithfully mimics the in vivo architecture and behavior of cells for use in drug screening and diagnostics.

SUMMARY

Described herein is a novel cell culture system also known as a disease-on-a-chip, which includes an apparatus and method for culturing non-neoplastic cells with and without neoplastic cells, which better mimics the in vivo architecture and therefore cell behavior. For example, a disease mimicking neoplastic cell culture, also known as tumor cell or cancer cell culture, of the invention comprises a population of cells that mimics the neoplastic cell population found in vivo. In one aspect the neoplastic cells used in the disease-on-a-chip may come from a patient from whom a tissue explant is obtained. This allows chemosensitivity and chemoresistivity testing that may be useful in predicting the effects of therapeutic agents on the tumor in vivo. Other aspects include using the device and method in high throughput assays for drug discovery. This allows for an accurate test to remove candidates that would provide a false positive or false negative in currently used cell culture systems that precede tests in animal models.

In one aspect the cell culture system comprises at least one hemichannel including a monolayer of non-neoplastic cells also known as normal cells. In one aspect the non-neoplastic cells are epithelial cells. In other aspects, the device comprises at least one hemichannel including a monolayer of non-neoplastic epithelial cells and neoplastic cells.

In one aspect a cell culture system is described comprising a planar member having at least one axis and thickness including at least one semicircular hemichannel extending in the direction of the at least one axis, with the at least one semicircular hemichannel partially formed into the thickness of the member; and a polymer layer in direct contact with the semicircular hemichannel to provide a substantially smooth surface, wherein the substantially smooth surface is configured to receive a plurality of cells.

In one aspect a cell culture system is described, comprising a planar member having at least one axis and thickness including at least one semicircular hemichannel extending in the direction of the at least one axis, wherein the planar member is configured to insert into a well plate, and the at least one semicircular hemichannel partially formed into the thickness of the member. The cell culture system further comprising a polymer layer in direct contact with the semicircular hemichannel to provide a substantially smooth surface, wherein the substantially smooth surface is configured to receive a plurality of cells.

In another aspect a method of generating a disease-on-a-chip is described comprising, providing a disease-on-a-chip apparatus comprising at least one semicircular hemichannel; providing non-neoplastic cells to grow in a monolayer on the hemichannels; providing at least one neoplastic cell or nodule of neoplastic cells to the single layer of non-neoplastic cells on the hemichannel; and providing a nutrient source for the cells to live.

In another aspect a method of manufacturing a cell culture system is described comprising, providing a planar surface, wherein the planar surface has at least one axis and a thickness; engraving at least one semicircular hemichannel into the planar surface; smoothing the at least one semicircular hemichannel by providing a polymer; and preparing the surface by coating with a cell attachment factor.

In another aspect a system for holding a disease-on-a-chip system in a well plate is described comprising, a well plate; a carrier plate; the disease-on-a-chip system; and a fastener plate.

BRIEF DESCRIPTION OF DRAWINGS

FIG. 14B is a magnification of a corner to better show the cell clumping.

FIG. 15A shows the rough surface of the semicircular hemichannel, and FIG. 15B shows cells clumping in the semicircular hemichannel with white outlines to help visualize the clumping and semicircular hemichannel boundaries.

FIG. 16A shows a smooth semicircular hemichannel and FIG. 16B shows a monolayer of cells along the smooth semicircular hemichannel with white outlines to visualize the monolayer and semicircular hemichannel boundaries.

FIG. 17A-FIG. 17C are images showing a monolayer of S1 polarized epithelial cells on a semicircular hemichannel, wherein FIG. 17A shows a monolayer of basoapical polarized S1 cells on a smooth semicircular hemichannel with a cell attachment factor, FIG. B is a magnification of a section of FIG. 17A where the white arrow indicates an apical tight junction identified using ZO1 marker, and FIG. 17C is an image of a monolayer of polarized S1 cells on a smooth semicircular hemichannel wherein the white arrows are identifying basal hemidesmosome marker alpha6-integrin.

FIG. 19A-FIG. 19C show images of neoplastic cells co-cultured with non-neoplastic cells in a cell culture system, with FIG. 19A showing a top view of a co-culture in the cell culture system with two points of interest highlighted with a dashed white line, FIG. 19B showing a side view of the top dashed line of FIG. 19A which only features a monolayer of non-neoplastic cells, and FIG. 19C is a side view of the bottom dashed line of FIG. 19A which shows a nodule of neoplastic cells growing with a monolayer of non-neoplastic cells.

DETAILED DESCRIPTION

Figure 1A:
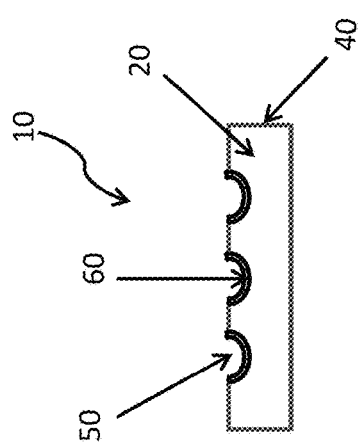
FIGS. 1A and 1B are cartoons that depict the general cell culture system, with FIG. 1A showing a cutaway of the cell culture system, and FIG. 1B showing a general cell culture system.
Figure 1B:
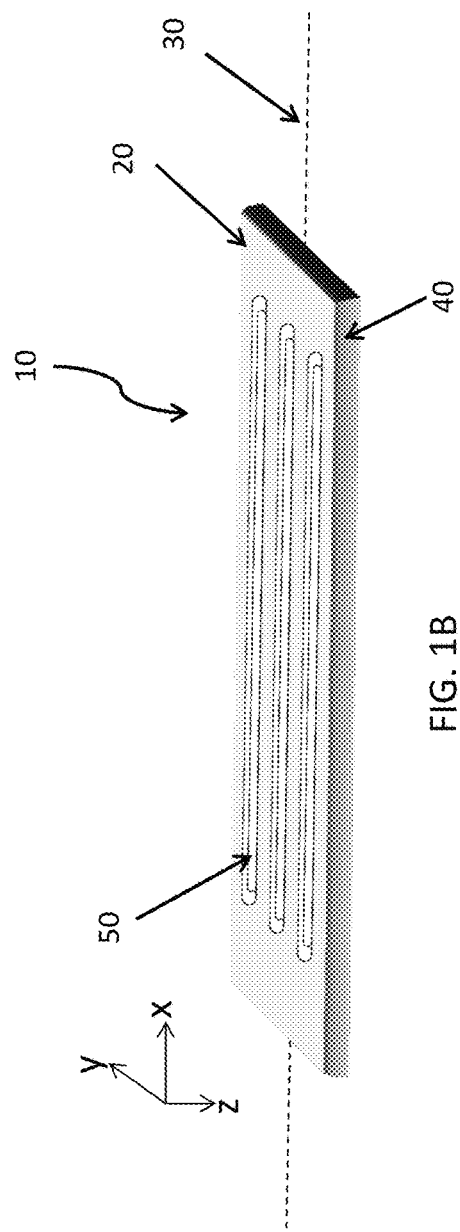

The invention described herein comprises a cell culture system, method of manufacture, and method of use, wherein the invention provides an environment which more faithfully mimics the in vivo environment of non-neoplastic and neoplastic cells. The present invention may provide better and more meaningful data than systems in the prior art. Referring now to FIGS. 1A and 1B, the system (10) comprises a planar member (20) having at least one axis (30) in the 'x' or 'y' plane and thickness (40) in the 'z' plane including at least one semicircular hemichannel (50) extending in the direction of the at least one axis, the at least one semicircular hemichannel partially formed into the thickness of the member. The present invention further comprises a polymer layer (60) in direct contact with the semicircular hemichannel to provide a substantially smooth surface, wherein the substantially smooth surface is configured to receive a plurality of cells.

A disease-on-a-chip system also known as a cell culture system in which neoplastic cells grow within an engineered phenotypically normal luminal epithelium or also referred to as a monolayer of non-neoplastic cells on a support comprising at least one semicircular hemichannel mimicking in vivo portions of a lumen or cavity is presented. In one aspect the lumen or cavity is representative of a duct. When grown on the disease-on-a-chip system, the non-neoplastic cells growing in vitro within the semicircular hemichannels are morphologically distinct from current cell culture systems which grow neoplastic and non-neoplastic cells on a flat surface. Moreover, neoplastic cells cocultured with a monolayer of non-neoplastic cells which are in direct contact with the semicircular hemichannels, display a different anticancer drug sensitivity compared to neoplastic cells cocultured with non-neoplastic cells on a flat surface and to monocultures of neoplastic cells on flat surfaces. The mimicry of tumor development with the non-neoplastic cells lining the semicircular hemichannels provides a platform for the design and testing of anticancer therapies in this system and may be modified for a high throughput system.

By "semicircular hemichannel" refers to a channel in the shape of a semicircle embedded or engraved into a planar member, wherein the widest part of the semicircle is on the surface of the planar member. Please refer to FIGS. 1A and 1B for an example.

By "neoplastic" refers to a state of a cell, wherein the cell is in the process of becoming or has already established itself as cancerous. This is classified by DNA modifications, epigenetic modifications, change in phenotype, or a change in proliferation activity.

By "non-neoplastic" refers to a cell that is not in the process of becoming or has not established itself as cancerous. This is classified by a lack of pertinent DNA modifications, a lack of pertinent epigenetic modifications, a lack of a pertinent change in phenotype, or a lack of change in proliferation activity.

The following Clauses are additional embodiments of the invention. These additional embodiments are described in detail below.

1. A cell culture system, comprising a planar member having at least one axis and thickness including at least one semicircular hemichannel extending in the direction of the at least one axis, with the at least one semicircular hemichannel partially formed into the thickness of the member; and a polymer layer in direct contact with the semicircular hemichannel to provide a substantially smooth surface, wherein the substantially smooth surface is configured to receive a plurality of cells.

2. The cell culture system of Clause 1, wherein the planar member comprises, acrylic, glass, plastic, PDMS or a combination thereof.

3. The cell culture system of Clause 1, wherein the plurality of cells are non-neoplastic cells.

4. The cell culture system of Clause 1, wherein the plurality of cells are non-neoplastic and neoplastic.

5. The system of Clause 3 and Clause 4, wherein the non-neoplastic cells are arranged in a monolayer.

6. The cell culture system of Clause 1, wherein the polymer layer includes a cell attachment factor 7. The cell culture system of Clause 6, wherein the cell attachment factor is laminin 111.

8. The cell culture system of Clause 1, wherein the at least one semicircular hemichannel has a width of up to 500 microns.

9. The cell culture system of Clause 1, wherein the at least one semicircular hemichannel has a width of between about 75 microns to about 120 microns.

10. The cell culture system of Clause 1, wherein the planar member further comprises domains of separate groups of semicircular hemichannels.

11. The cell culture system of Clause 10, wherein the domains are separated by a spacer.

12. The cell culture system of Clause 11, wherein the spacer comprises acrylic, glass, plastic, or a combination thereof.

13. The cell culture system of Clause 10, wherein the planar member comprises up to 1,560 separate domains.

14. The cell culture system of Clause 10, wherein the planar member comprises up to 96 separate domains.

15. The cell culture system of Clause 1, wherein the length of the planar member is about 127 millimeters to about 128 millimeters.

16. The cell culture system of Clause 1, wherein the length of the planar member is up to 500 millimeters.

17. The cell culture system of Clause 1, wherein the length of the planar member is at least 1.5 millimeters.

18. The cell culture system of Clause 1, wherein the width of the planar member is about 85 millimeters to about 86 millimeters.

19. The cell culture system of Clause 1, wherein the width of the planar member is up to 500 millimeters.

20. The cell culture system of Clause 1, wherein the at least one semicircular hemichannel does not extend to the edge of the planar member.

21. The cell culture system of Clause 20, wherein the length between the at least one semicircular hemichannel and the edge of the planar member is at least 20 microns.

22. The cell culture system of Clause 1, wherein the system is configured to interact with a cell culture robot.

23. A cell culture system, comprising: a planar member having at least one axis and thickness including at least one semicircular hemichannel extending in the direction of the at least one axis, wherein the planar member is configured to insert into a well plate, the at least one semicircular hemichannel partially formed into the thickness of the member; and a polymer layer in direct contact with the semicircular hemichannel to provide a substantially smooth surface, wherein the substantially smooth surface is configured to receive a plurality of cells.

24. The cell culture system of Clause 23, wherein the planar member is up to 10,000 microns in length.

25. The cell culture system of Clause 23, wherein the planar acrylic member includes up to 100 semicircular hemichannels.

26. The cell culture system of Clause 23, wherein the at least one semicircular hemichannel has a width of up to 500 microns.

27. The cell culture system of Clause 23, wherein the at least one semicircular hemichannel has a width of between about 75 microns to 120 microns.

28. The cell culture system of Clause 23, wherein the planar member comprises acrylic, glass, plastic, or a combination thereof.

29. The cell culture system of Clause 23 wherein the cell culture system is configured to interact with a cell culture robot.

30. The cell culture system of Clause 23, wherein the polymer includes a cell attachment factor.

31. The cell culture system of Clause 30, wherein the cell attachment factor is laminin 111.

32. The cell culture system of Clause 23, wherein the plurality of cells are non-neoplastic cells.

33. The cell culture system of Clause 23, wherein the plurality of cells are non-neoplastic and neoplastic cells.

34. The cell culture system of Clause 32 and 34, wherein the non-neoplastic cells are arranged in a monolayer.

35. The cell culture system of Clause 4 and Clause 33, wherein the non-neoplastic cells are provided as individual cells or a nodule.

36. A method of generating a disease-on-a-chip comprising; providing a disease-on-a-chip apparatus comprising at least one semicircular hemichannel; providing non-neoplastic cells to grow in a monolayer on the hemichannels; providing at least one neoplastic cell or nodule of neoplastic cells to the single layer of non-neoplastic cells on the hemichannel; and providing a nutrient source for the cells to live.

37. The method of Clause 36, wherein the neoplastic cell or nodule of neoplastic cells comes from a mammalian cancer that originates or proliferates in a spherical channel or lumen in the mammalian body.

38. The method of Clause 37, wherein the at least one neoplastic cell or nodule of neoplastic cells comes from mammalian prostate cancer, colon cancer, cancer of a bile duct, pancreatic cancer, cancer of a salivary gland, ovarian cancer, lung cancer, or breast cancer.

39. The cell culture system of Clause 5 and Clause 34, wherein the non-neoplastic cells are epithelial in origin.

40. A method of manufacturing a cell culture system comprising: providing a planar surface, wherein the planar surface has at least one axis and a thickness; engraving at least one semicircular hemichannel into the planar surface; smoothing the at least one semicircular hemichannel by providing a polymer; and preparing the surface by coating with a cell attachment factor.

41. The method of manufacture of Clause 40, wherein the engraving is performed by a laser.

42. The method of manufacture of Clause 40, wherein the semicircular hemichannel shape is achieved by adjusting the focus of the laser.

43. The method of manufacture of Clause 40, wherein the diameter of the semicircular hemichannel is controlled in part by the laser intensity.

44. The method of manufacture of Clause 40, wherein the polymer layer comprises polymethyl methacrylate (PMMA).

45. The method of manufacture of Clause 40, wherein the polymer is applied by spin coating.

46. The method of manufacture of Clause 40, wherein the member is treated with air plasma after smoothing the at least one semicircular hemichannel and before preparing the surface with a cell attachment factor.

47. The method of manufacture of Clause 40, wherein the cell attachment factor is laminin 111.

48. A system for holding a disease-on-a-chip system in a well plate comprising: a well plate; a carrier plate; the disease-on-a-chip system; and a fastener plate.

49. The system of Clause 48, wherein the well plate comprises between 6 and 1,536 wells.

50. The system of Clause 48, wherein the carrier plate and fastener plate are made of plastic.

51. The system of Clause 48, wherein the disease-on-a-chip system is placed inside the carrier plate, and wherein the carrier plate can be removed from the well plate for analyses.

52. The system of Clause 48, wherein the fastener plate includes holes that align over each well in the well plate.

53. The system of Clause 52, wherein the system is configured to allow for optical visualization of the disease-on-a-chip system without removing the system from the well plate.

The present invention comprises a planar member also known as a support, having at least one axis and thickness including at least one semicircular hemichannel extending in the direction of the at least one axis, the at least one semicircular hemichannel partially formed into the thickness of the member. The planar member may be of any shape including circle, square, rectangle, triangle, a polygon, dog bone, etc. Preferably, the shape is a circle, square or rectangle. The length and width of the planar member may be up to about 500 millimeters in length from end to end as a rectangle, or up to about 500 millimeters in diameter as a circle. In some aspects the length or diameter is at least about 1.5 millimeters. In other embodiments, the length of a rectangular planar member is between about 127 millimeters to about 128 millimeters. In some aspects of that embodiment, the width is between about 85 to about 86 millimeters. The planar member may be comprised of acrylic, glass, plastic, polymer, PDMS, or a combination thereof. In one aspect, the planar member is made from a material that is transparent.

Figure 28:
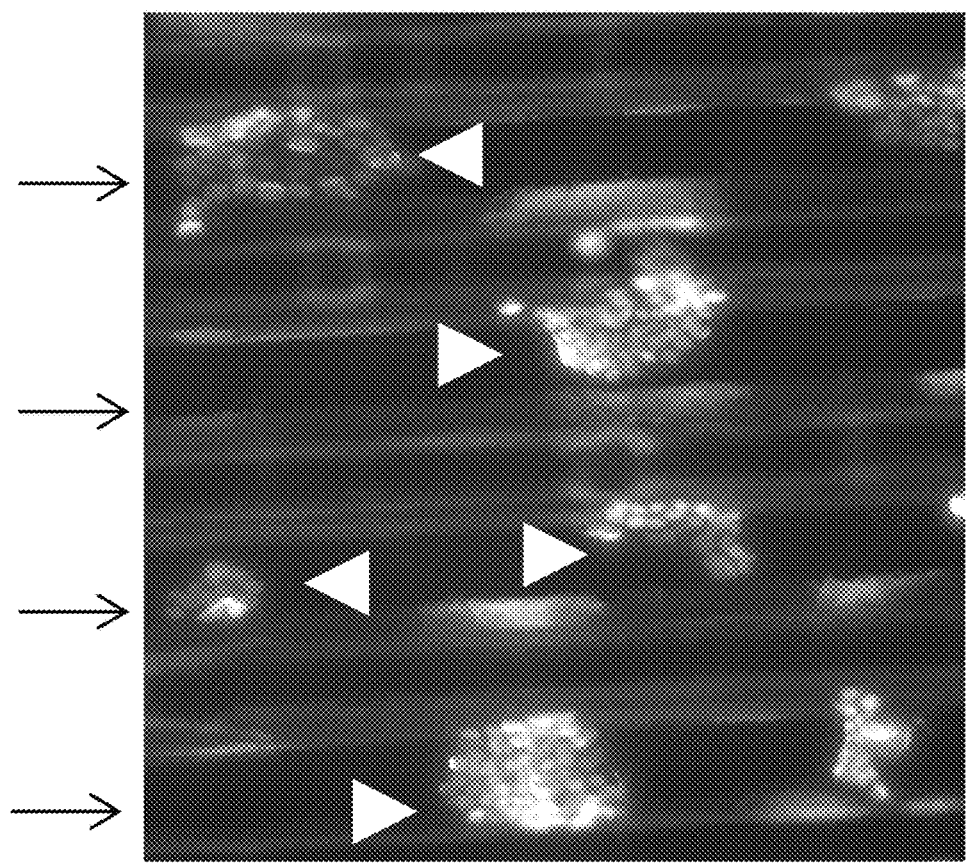
FIG. 28 is an image of a plurality of semicircular hemichannels growing tumors on a monolayer of epithelial non-neoplastic cells, where the black arrows indicate individual semicircular hemichannels and the white arrows indicate tumors.

Referring now to FIG. 1, within the planar member includes at least one semicircular hemichannel. In some aspects the planar member may comprise a plurality of semicircular hemichannels as shown in FIG. 1B and FIG. 28. The semicircular hemichannel forms a valley within the planar member and is about the shape of a half circle within the planar member. The widest width of the semicircular hemichannel, which is found at the top of the hemichannel, or at the surface of the planar member, may be up to 500 microns in length. In other aspects the width of the semicircular hemichannel at the surface of the planar member is between about 75 microns to about 120 microns. In other aspects the width of the semicircular hemichannel is about 100 microns. The length of the channel will depend on the length, width, or diameter of the planar membrane. The semicircular hemichannel may traverse across the entire length of the planar member, or the semicircular hemichannel may not reach the edge of the planar member resulting in a boarder at the planar member's edge of sorts where no hemichannel exists. This border may be between 1 micron and 50 microns from the planar member's edge. In other aspects, the border is at least 20 microns in length from the planar member's edge to the nearest semicircular hemichannel. The depth and width of the semicircular hemichannel is controlled by the manufacturing process, described below. The semicircular hemichannel's geometry is designed to mimic half a lumen or a cavity found in vivo.

Figure 2:
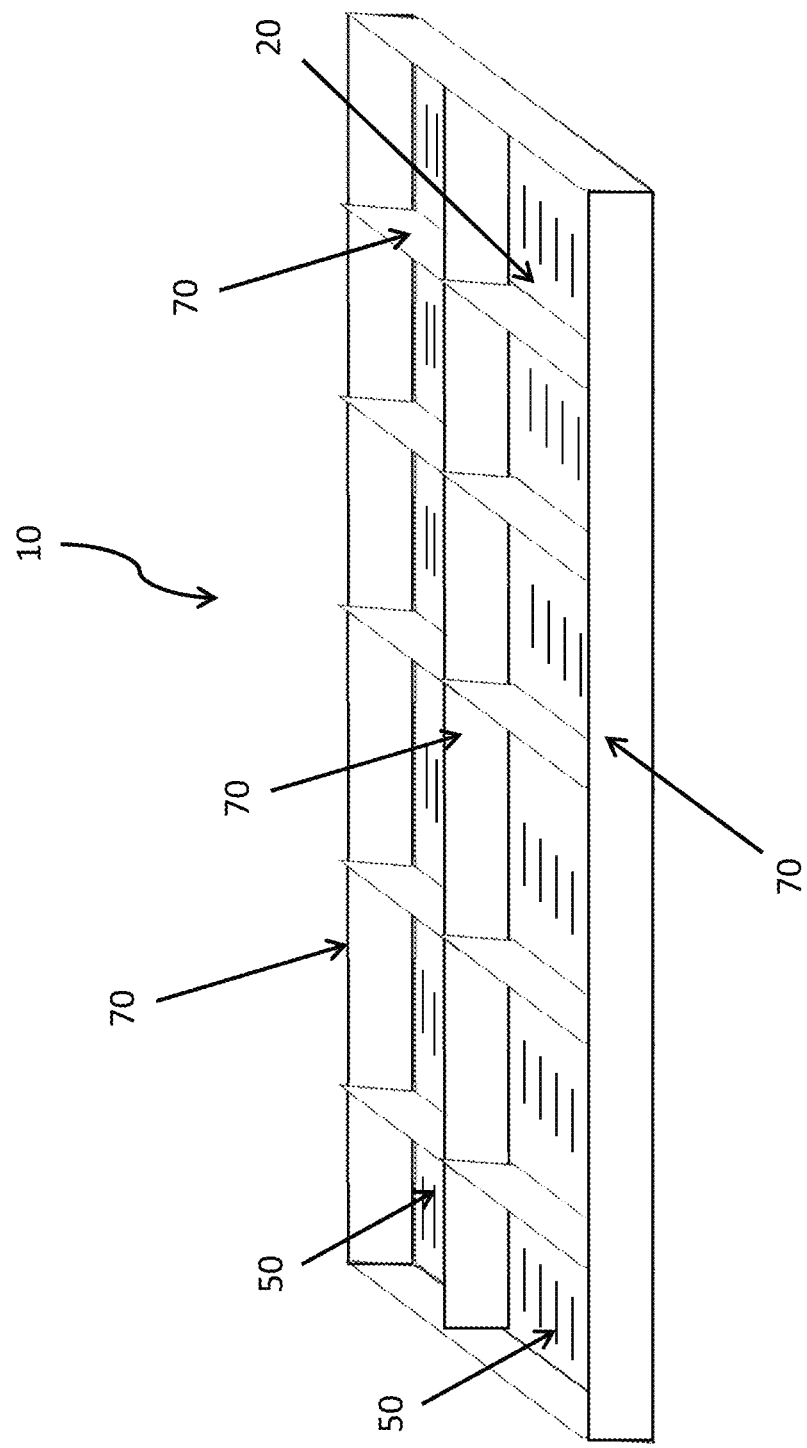
FIG. 2 is a cartoon showing a general scheme of a high throughput cell culture system with different domains and including spacers.
Figure 3:
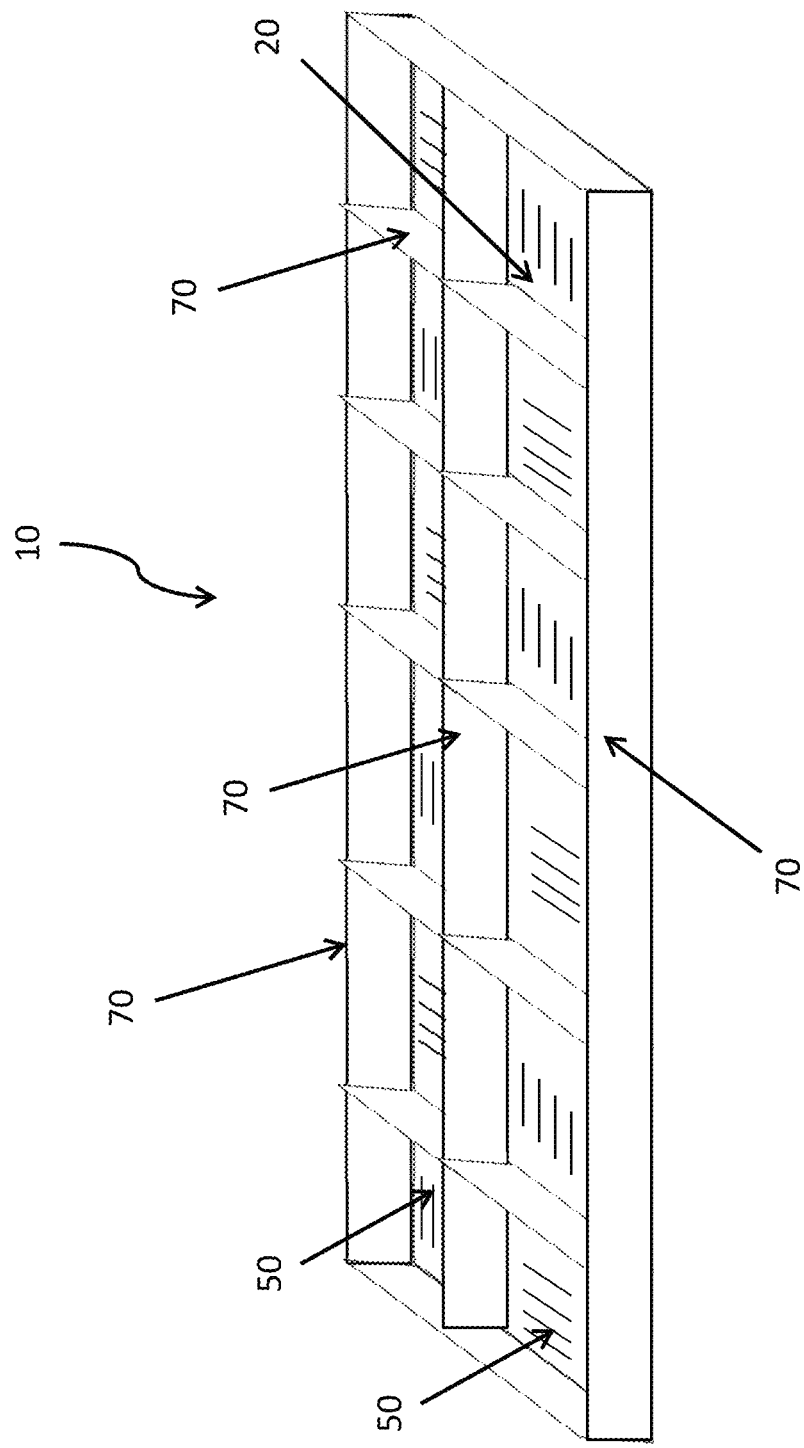
FIG. 3 is a cartoon showing a general scheme of a high throughput cell culture system including spacers, and wherein the semicircular hemichannels in separate domains run in different directions along an axis.
Figure 5:
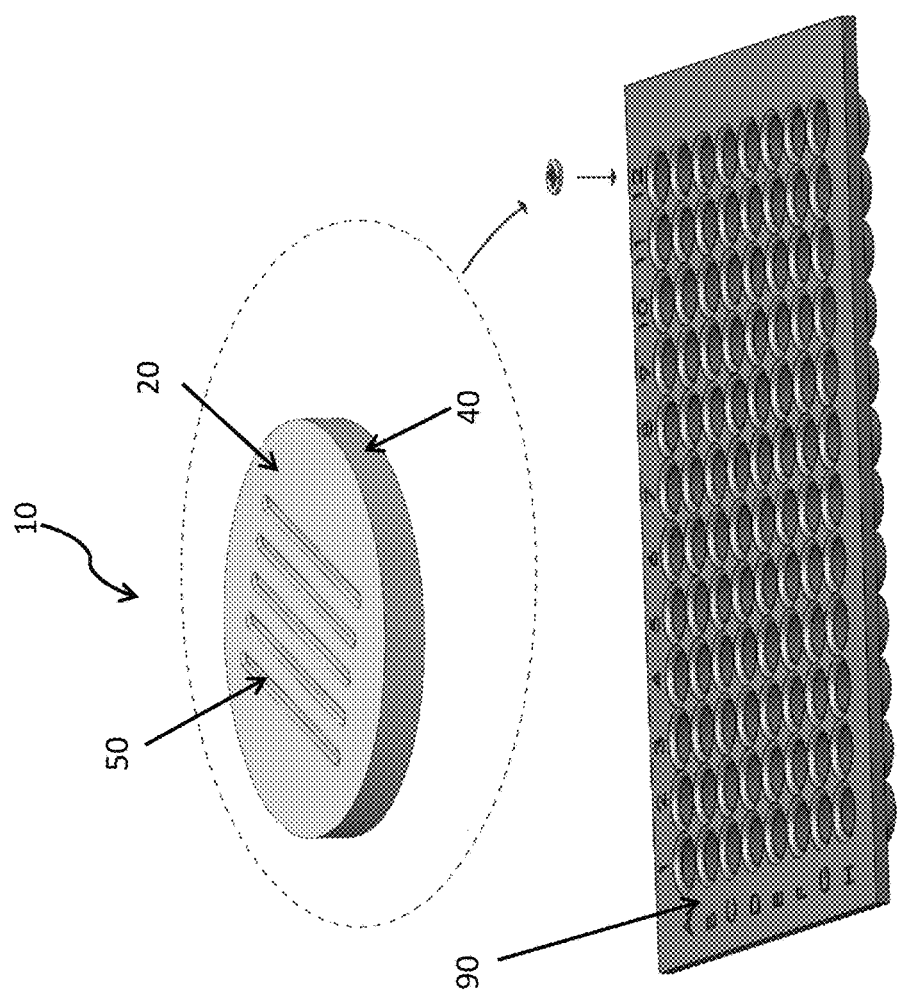
FIG. 5 is a cartoon showing a cell culture system which operably couples with a housing.
Figure 6:
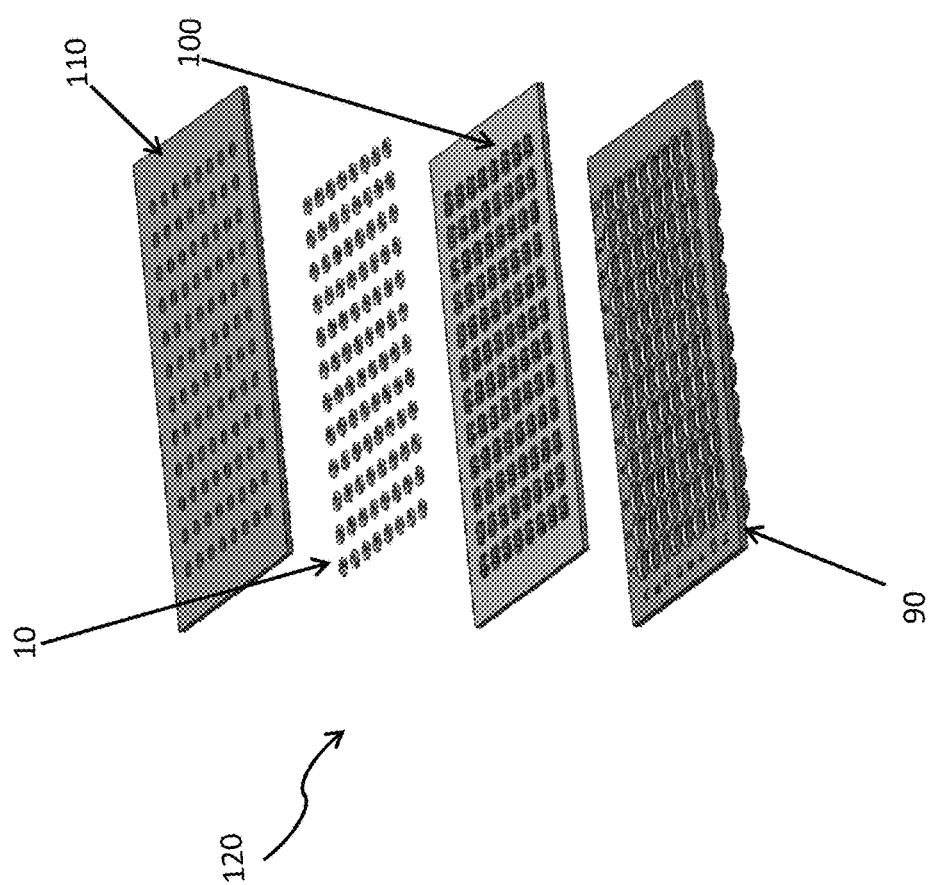
FIG. 6 is a cartoon showing an example of a high throughput system wherein the cell culture system is operably coupled to a holder device, which is then operably coupled to ahousing.
Figure 7:
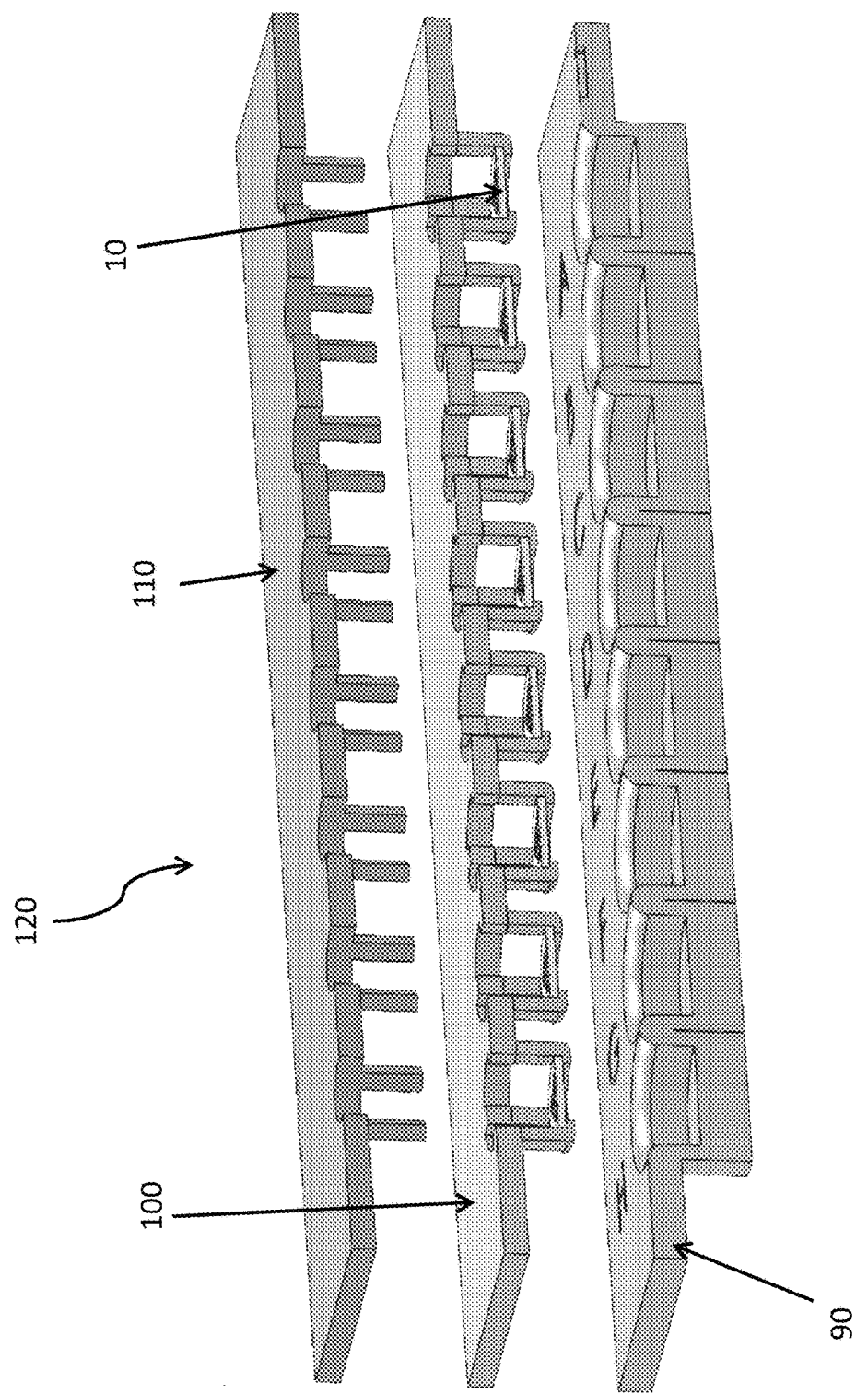
FIG. 7 is a cut away and separated view of an example of a high throughput system wherein a holder device is operably coupled to a cell culture system, and wherein the holder device is operably coupled to a housing.
Figure 8:
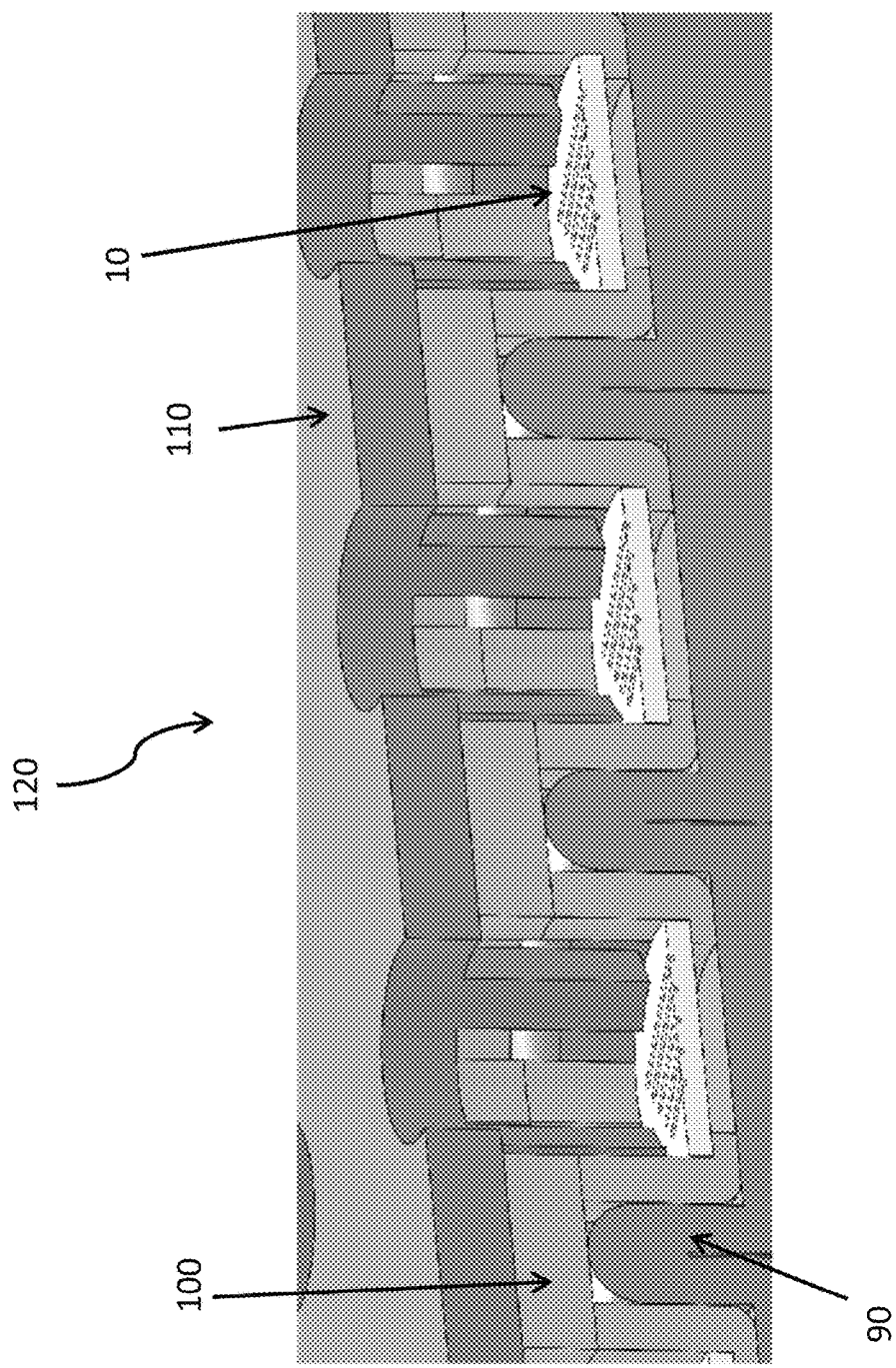
FIG. 8 is a cut away view of an example of a high throughput system wherein the a holder device is operably coupled to a cell culture system, and wherein the holder device is operably coupled to a house.
Figure 9:
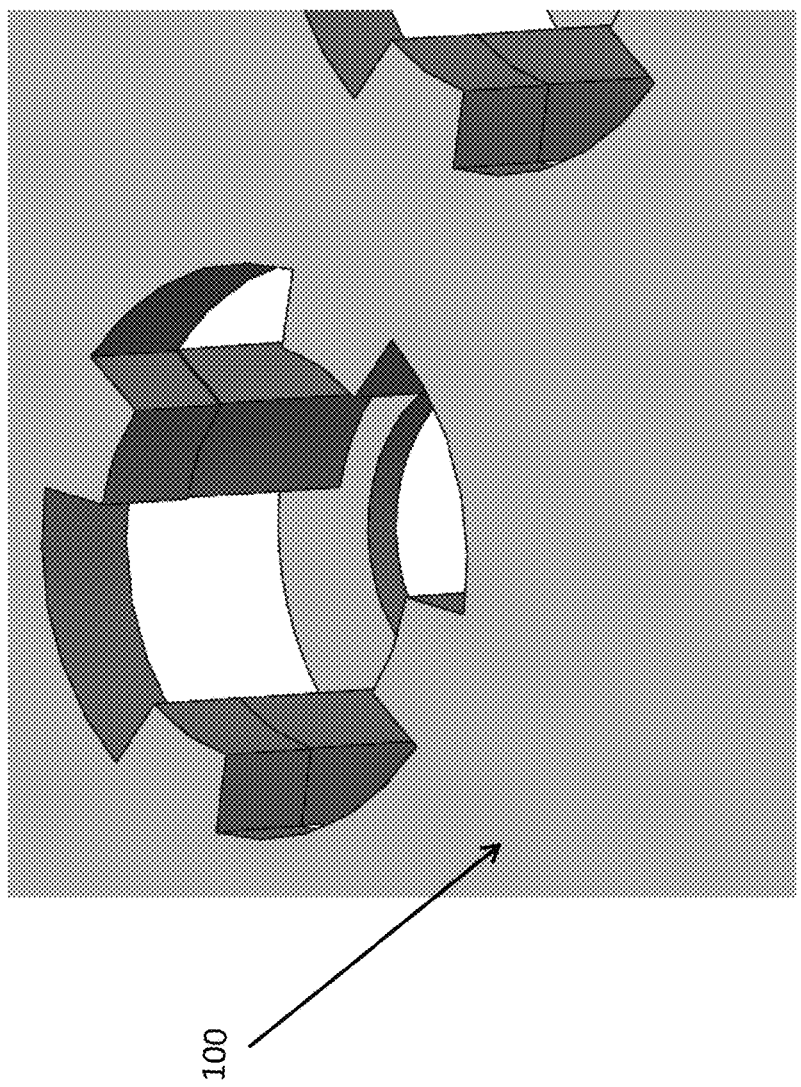
FIG. 9 is a top view of an example of a carrier plate, which may be a component of a holder device.
Figure 10:
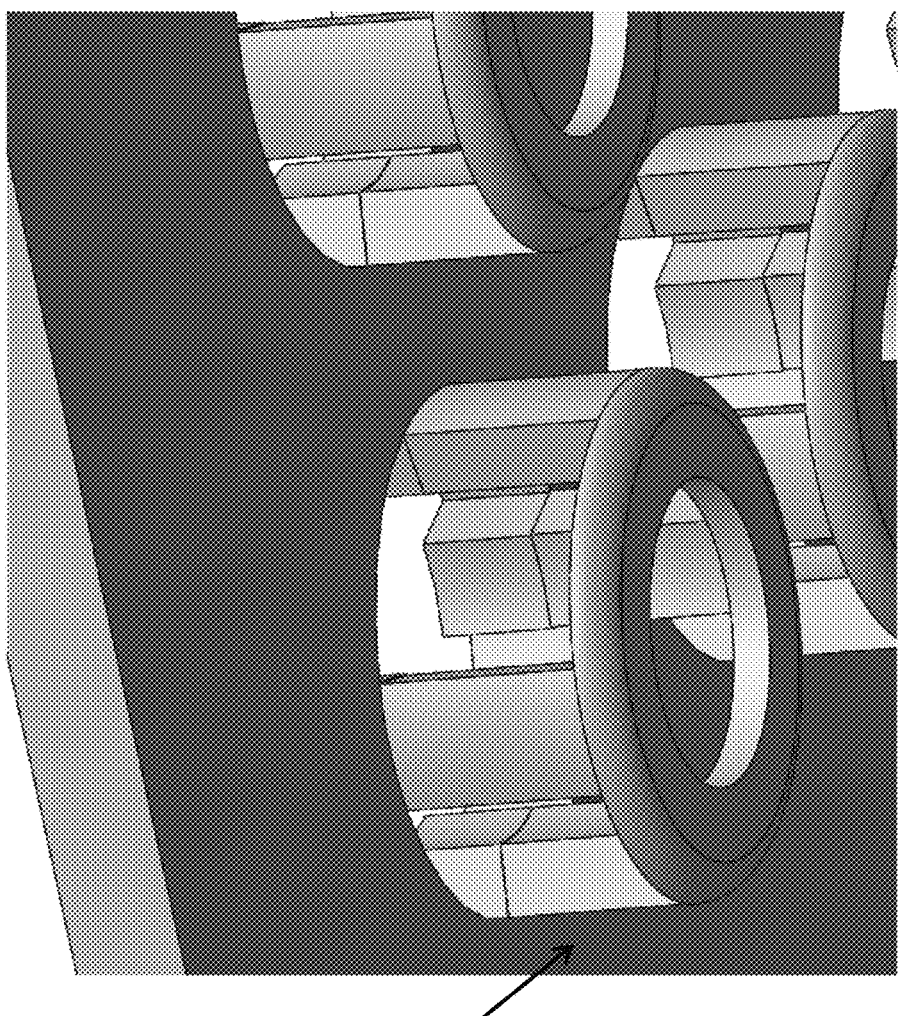
FIG. 10 is a bottom view of an example of a carrier plate, which may be a component of a holder device.
Figure 11:
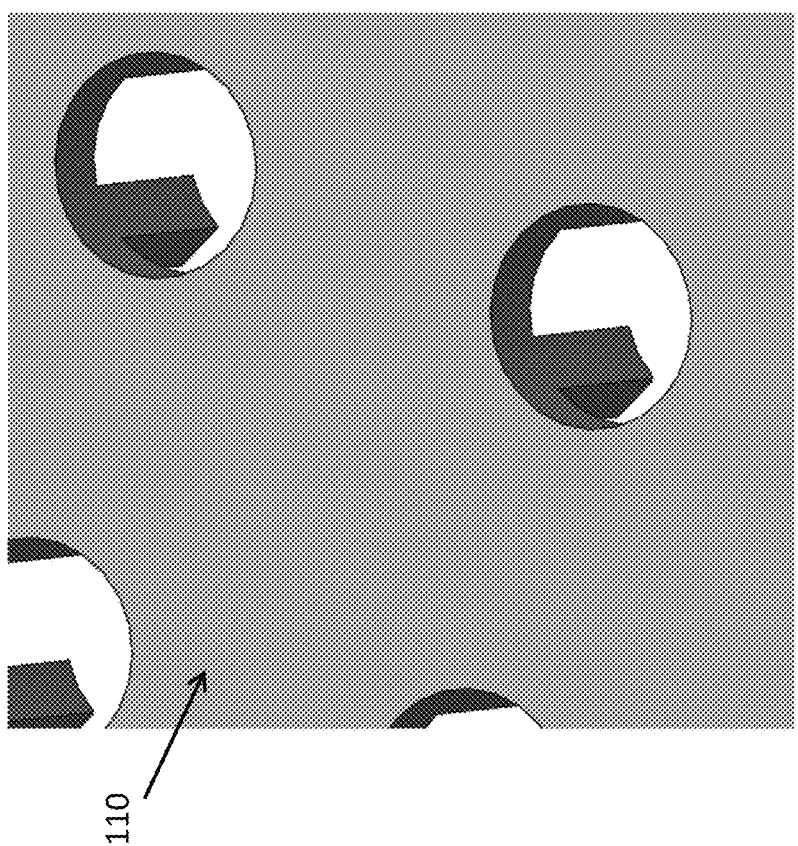
FIG. 11 is a top view of an example of a fastener plate, which may be a component of a holder device.
Figure 12:
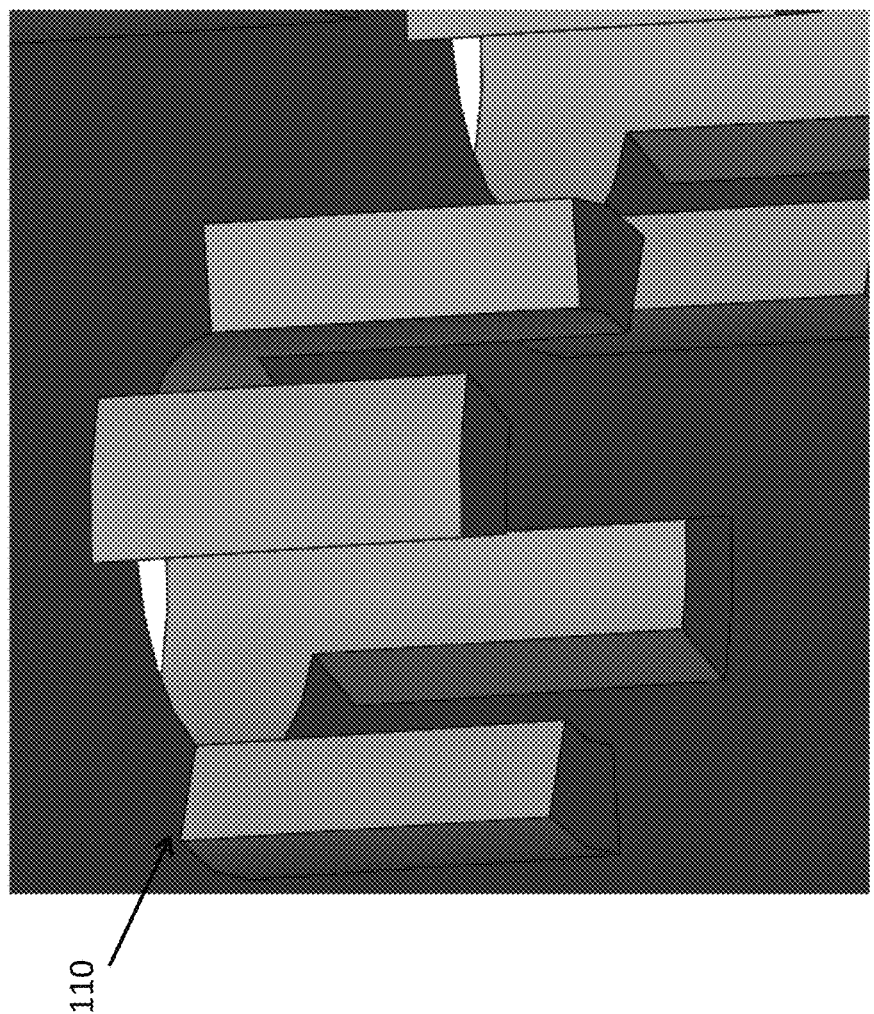
FIG. 12 is a bottom view of an example of a fastener plate, which may be a component of a holder device.
Figure 13:
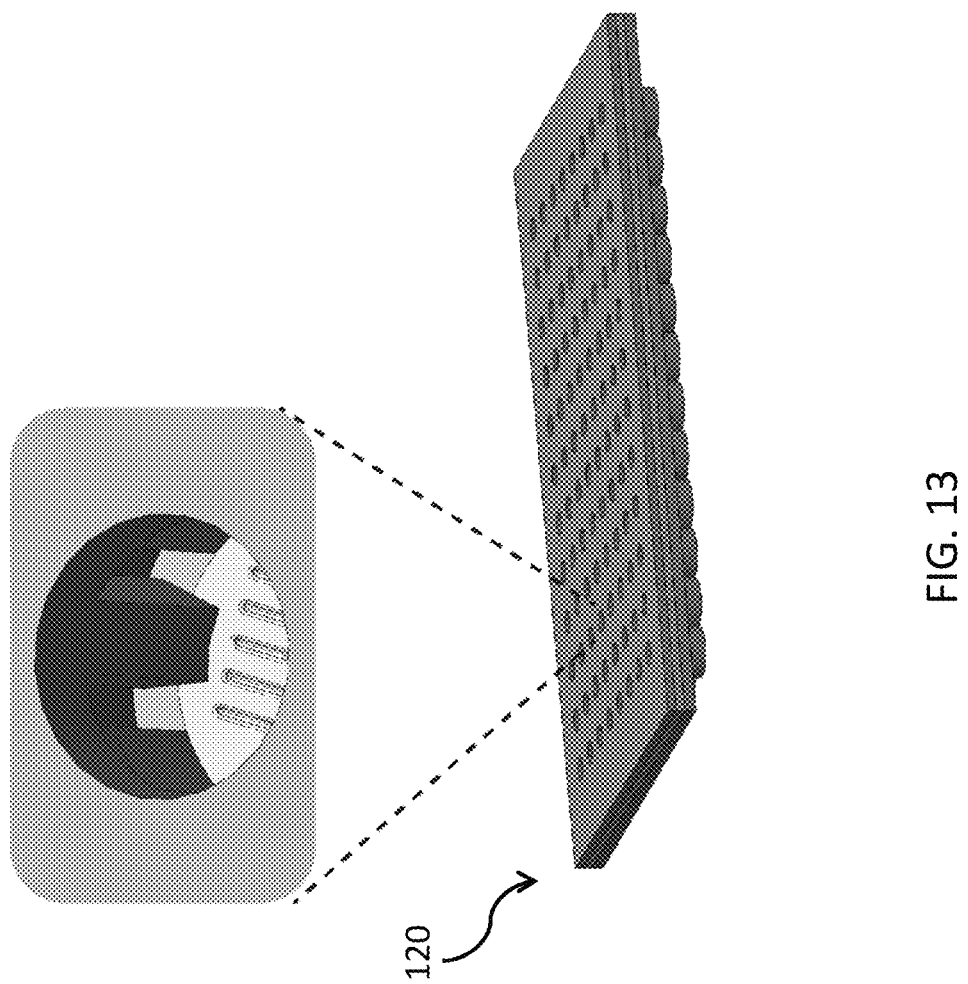
FIG. 13 is an image of a holder device operably coupled to a housing, and the dashed lines represent a magnified view of a cell culture system held in place by the holder device.

A planar member comprises at least one semicircular hemichannel. A planar member may be divided into separate domains, which comprise a plurality of semicircular hemichannels. The hemichannels in each domain may traverse a domain space in the same direction. However, each domain may change the direction of traversal for its plurality of semicircular hemichannels, making it easier for analysis. In some aspects, a planar member may have up to 1,560 separate domains. In other aspects, the planar member includes at least two domains. It may be desirable to have 96 separate domains on one planar member. A spacer may be present to separate each domain. By "spacer" refers to a physical separation between at least two domains. This may be made of any number of materials and may be as tall and as thick as necessary. Referring now to FIG. 2 and FIG. 3, in one aspect a spacer (70) is a piece of material comprising of plastic, glass, polymer, acrylic, PDMS, or a combination thereof, which physically separates the domains from each other. The spacers also serve as boundaries for holding in liquids such as media and liquid delivery of pharmaceutical drugs, and keeping such liquids and pharmaceutical drugs from interacting with the other domains. The spacers may run around the boarder of the planar device and between the domains effectively providing walls and a means of separation for cell culturing. The spacer may be a straight rectangular component that is placed about 90° or perpendicular to the surface of the planar member. A spacer may have a width of up to about 1 mm. A spacer may have a width of at least 100 microns. In other aspects, the planar member does not have any spacers, because the planar member fits inside a housing (90) which effectively can hold in liquid as shown in FIG. 5. An example of a housing would be a well in a multiwell plate. By "mutli well plate" refers to a cell culture system having a flat plate and at least two circular wells, wherein the separate wells allows for culturing separate groups of cells at the same time. Multiwell plates are commercially available through several manufacturers. The planar member and semicircular hemichannel arrangement may be configured to operably couple with a cell culture robot. By "cell culture robot" refers to an automated machine which is programed to dispense a preselected amount of liquid in a preselected location. Examples only, and by no means an endorsement or a suggestion of best mode, of a cell culture robot include MACCS AUTOMATED CELL CULTURE SYSTEM or CELLMATE culture robot. More information on this type of automated device may be found in U.S. Pat. No. 7,816,128.

For certain applications it is desirable to generate a cell culture system also known as a disease-on-a-chip which is a high throughput system, such as drug discovery and screening for example. In a high throughput system maximizing the number of cell culture systems or semicircular hemichannels that can be analyzed at one time and the ability to screen a large amount of pharmaceutical drug or lead candidate is key. One way to generate this system is to design a planar member having a plurality of semicircular hemichannels as shown in FIG. 1B and FIG. 28. In some aspects the high throughput system further including groups of the plurality of semicircular hemichannels separated into domains, and the domains are separated by spacers as shown in FIG. 2 and FIG. 3. Another way to generate a high through put system is to generate circular planar members having a plurality of semicircular hemichannels, which can fit or insert into a housing such as a multiwell plate as shown in FIG. 5. In the embodiment of inserting a planar member into a housing each circular planar member has its own plurality of semicircular hemichannels.

Figure 15A:
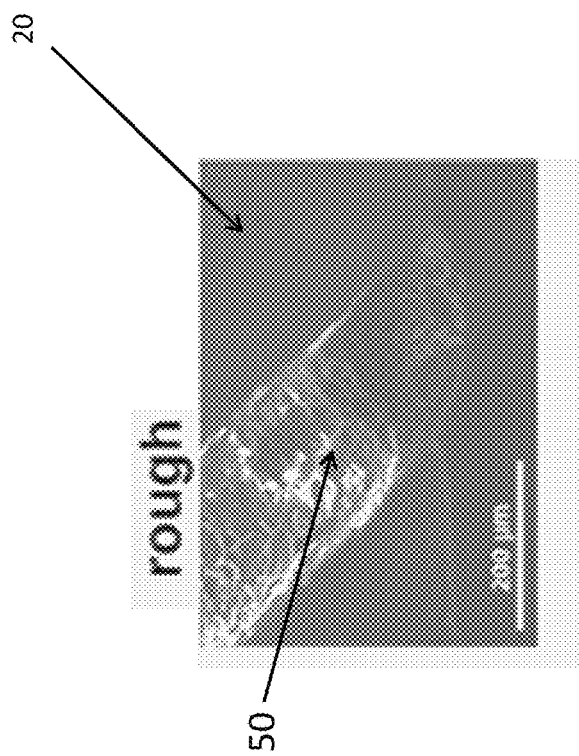
FIG. 15A and FIG. 15B show images of a rough semicircular hemichannel, where
Figure 15B:
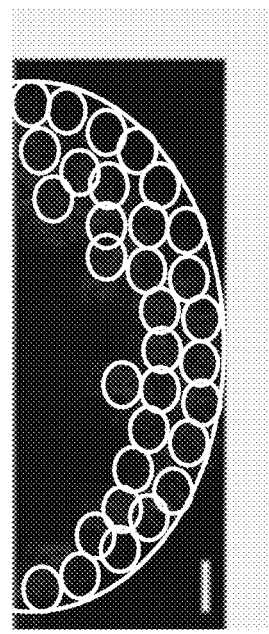
Figure 16A:
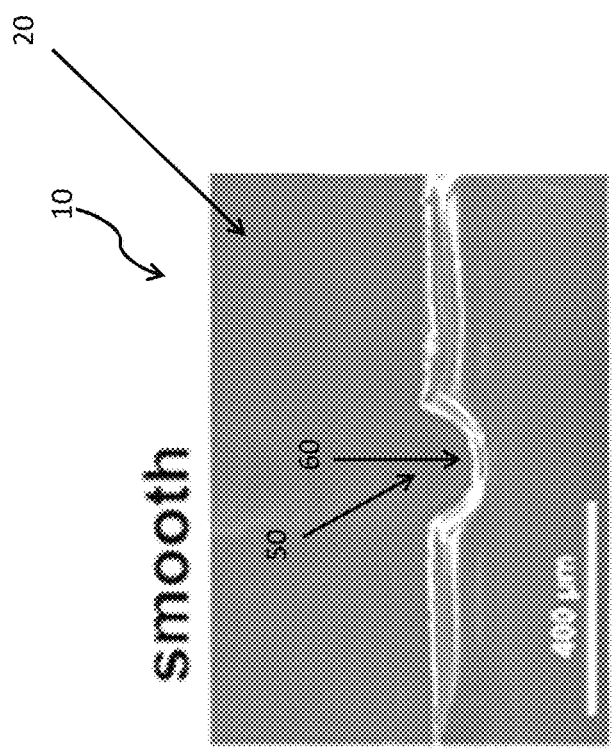
FIG. 16A and FIG. 16B show images of a smooth semicircular hemichannel, where
Figure 16B:
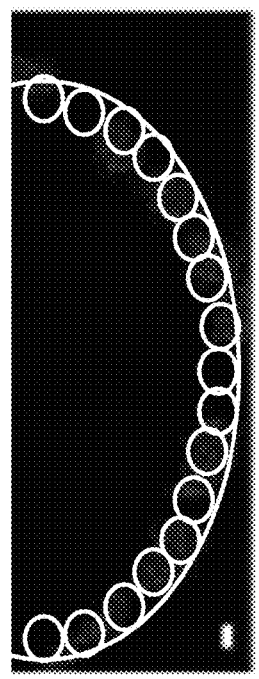
Figure 17A:
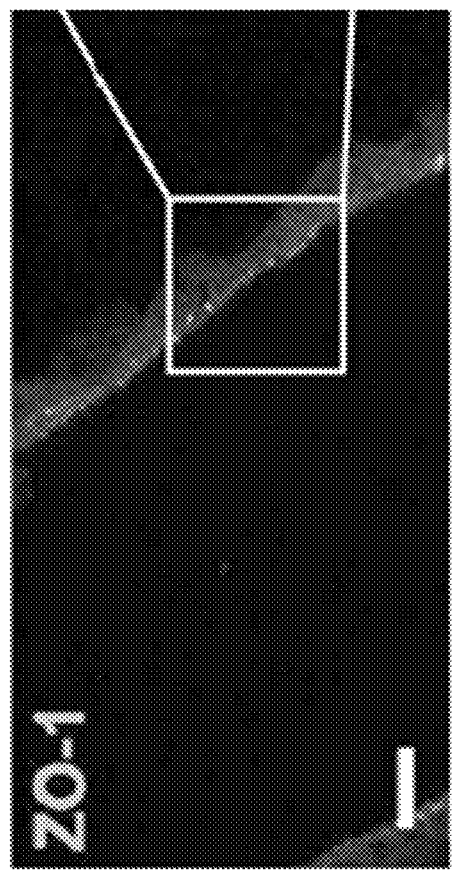
Figure 17B:
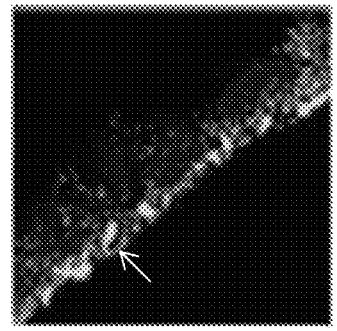
Figure 17C:
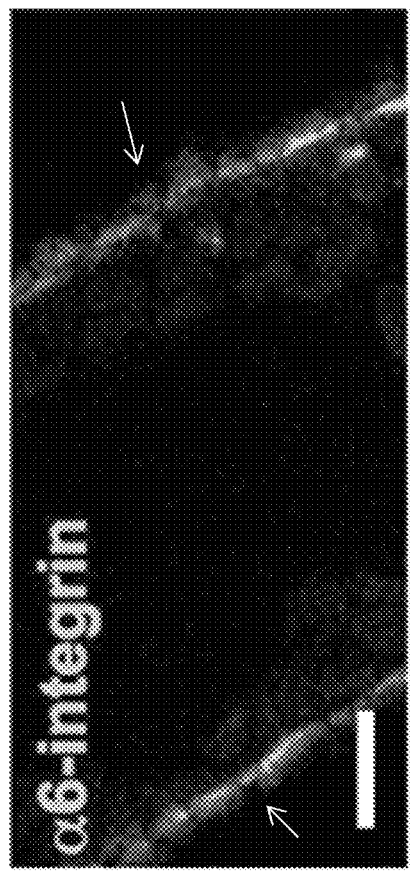

An exemplary method of manufacture includes using a laser to micromachine acrylic-based hemichannels with a circular cross section generating semicircular hemichannels. This method has high development efficiency (cost/time ratio) and offers the flexibility of adjusting the semicircular hemichannels' depth and length across the chip. In one embodiment, semicircular hemichannels are engraved on acrylic sheets using a $CO_2$ laser cutting and engraving system operating in continuous wave mode at about 30 watts power and about 1 mm/ms. Other materials including plastic, polymer, glass, PDMS, or combinations thereof are also acceptable for use in this process. In other embodiments, glass may be etched to generate the semicircular hemichannel using etching methods known in the art. Focusing the laser on the acrylic surface yielded V-shaped cross-sections. To achieve semicircular cross-sections, the laser may be focused between about 0.5 mm to about 1 mm above the surface. This distance may be altered to change the diameter of the semicircular hemichannel. For instance, V-shaped hemichannels may be obtained by reducing this distance whereas larger, round, channels may be obtained by augmenting this distance. Rough surfaces obtained after laser micromachining promoted cell growth as multilayers rather than the desired single-layer coating or monolayer of cells on the semicircular hemichannel usually found in vivo as shown in FIG. 15A and FIG. 15B. This issue or a rough surface was solved by smoothing the surfaces by coating a polymer onto the roughened surface as shown in FIG. 16A and FIG. 16B. By "polymer" refers to a molecule or macromolecule that is composed of repeating subunits. The polymer may be applied by spin coating, dipping, or other methods known in the art. An example of a polymer that may be used is polymethyl methacrilate (PMMA). Optionally, treating the planar member having at least one semicircular hemichannel with air plasma increased hydrophilicity, as observed from water contact angle measurements, which facilitated coating with a cell attachment factor. Examples of cell attachment factors include laminin 111, RGD peptides, antibodies, antibody fragments, collagens, extra cellular matrix (ECM) components, or a combination thereof.

The cell culture system and method may be used to study and recreate an in vivo geometry or environment using non-neoplastic cells which form the exposed layer in a cavity or a lumen within a body. By "lumen" refers to the interior space of a tubular structure, such as but not limited to arteries, intestines, fallopian tubes, ducts, or glands. In certain aspects, the non-neoplastic cells are epithelial cells. These cell types originate from the endoderm and ectoderm during biological development. Epithelial cell types are found in ducts, stomach, intestines, glands, lymph system, blood vessels and arteries, veins, prostate, colon, fallopian tubes, bladder, salivary glands, lungs, and ovary. The cell types of interest form a monolayer within the body. The non-neoplastic cells are placed in the semicircular hemichannels forming a monolayer as shown in FIG. 16B and FIG. 19B. The non-neoplastic cells form a monolayer within the semicircular hemichannel by interacting with a substantially smooth polymer layer coated on the semicircular hemichannel. Further, the substantially smooth surface provided by the polymer layer may include cell attachment factors. In this aspect, the semicircular hemichannel is coated with a polymer layer and includes cell attachment factors which may be partially incorporated into the polymer layer, and then a monolayer of non-neoplastic cells in contact with the polymer/cell attachment factor layer. By "cell attachment factor" refers to a factor that promotes the attachment of a cell. Examples of an attachment factor could be ligands, peptides, proteins, protein fragments, antibodies, antibody fragments, synthetic peptides, synthetic proteins, adhesives, or biomolecules. By "biomolecule" refers to any product produced by a cell. The type of epithelial cell that is grown in the cell culture system determines the lumen or cavity type that is being mimicked.

Neoplastic cells are seeded on top of the non-neoplastic cell layer. The neoplastic cells form into tumors or also referred to as nodules. By "nodule" refers to a collection of at least three cells or a mass ranging in size from about 30 microns to about 100 microns in diameter. The neoplastic cells that may be used in this system are cancers that may originate in the structure being mimicked (i.e. a lumen or a cavity), or may be secondary tumors that form from other locations that have metastasized and begin proliferating in the structure of the body that is being mimicked. Examples of cancers that may be studied are the different histological and molecular types of breast cancers, lung cancers, brain cancers, prostate cancers, pancreatic cancers, ovarian cancers, melanomas, stomach cancers, mouth cancers, intestinal cancers, bone cancers, lymphomas, leukemias, anal cancers, adrenal cancers, bile duct cancers, bladder cancers, cancers of unknown primary location, cervical cancers, endometrial cancers, esophagus cancers, eye cancers, gall bladder cancers, gastrointestinal carcinoid tumors, gestational trophoblastic diseases, hodgkin diseases, Kaposi sarcomas, kidney cancers, laryngeal and hypopharyngeal cancers, liver cancers, mesotheliomas, multiple myelomas, nasal cavity and paranasal sinus cancers, nasopharyngeal cancers, neuroblastomas, glioblastomas, non-hodgkin lymphomas, oral cavity cancers, osteosarcomas, pituitary tumors, retinoblastomas, rhabdomyosarcomas, sarcomas, skin cancers, small intestine cancers, testicular cancers, thymus cancers, thyroid cancers, uterine sarcomas, vaginal cancers, vulvar cancers, waldenstrom macroglobulinemia, wilms tumors, fibrosarcomas, and liposarcomas.

Described is an exemplary embodiment for growing cells and co-culture of non-neoplastic and neoplastic cells on the cell culture system. To begin, an epithelial cell type is seeded onto a semicircular hemichannel and grown until a monolayer of epithelial cells has formed on the semicircular hemichannel. Then neoplastic cells are seeded as groups of cells or nodules using between 3 and 100 cells to seed on top of the monolayer of epithelial cells. Co-culture the cells using the appropriate media and conditions. At a point when the neoplastic cells are established and have grown three-dimensional tumors, analysis and assays may be performed. The conditions needed for this co-culturing including, incubation, media, gas levels are known in the art and may be easily discerned without undue experimentation. The types of assays that may be run include but are not limited to molecular pathway studies, inhibition studies, toxicology studies, development studies, and lead molecule identification studies.

Figure 23:
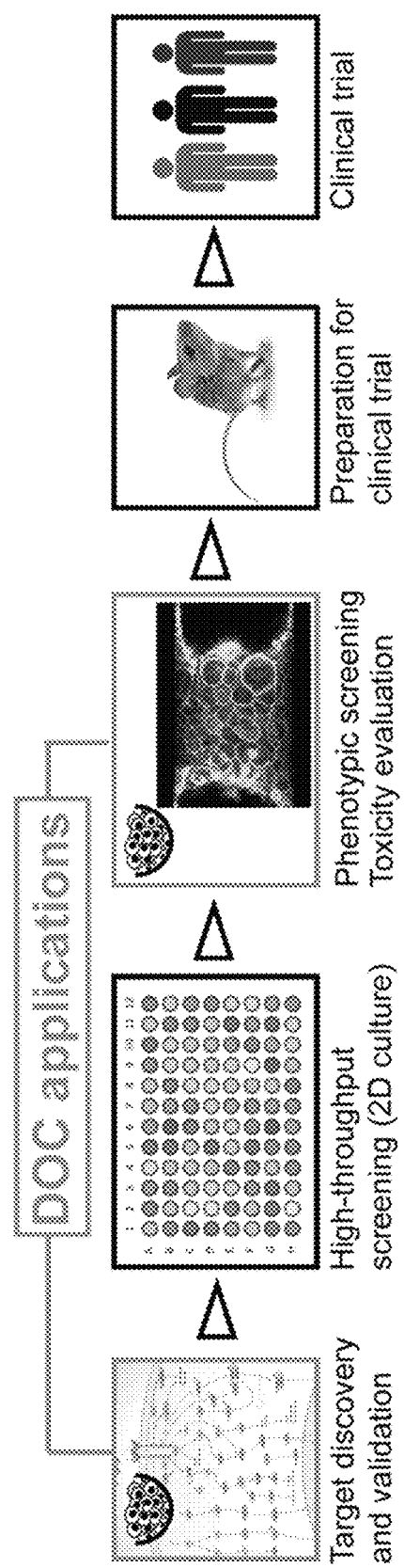
FIG. 23 shows a general drug discovery process from lead molecule identification up to human trials, and identifying that the disease-on-a-chip or cell culture system may be used in several applications in this process including to identify a lead molecule and perform phenotypic high throughput screening/toxicity evaluation, or both prior to going into an animal model.
Figure 24:
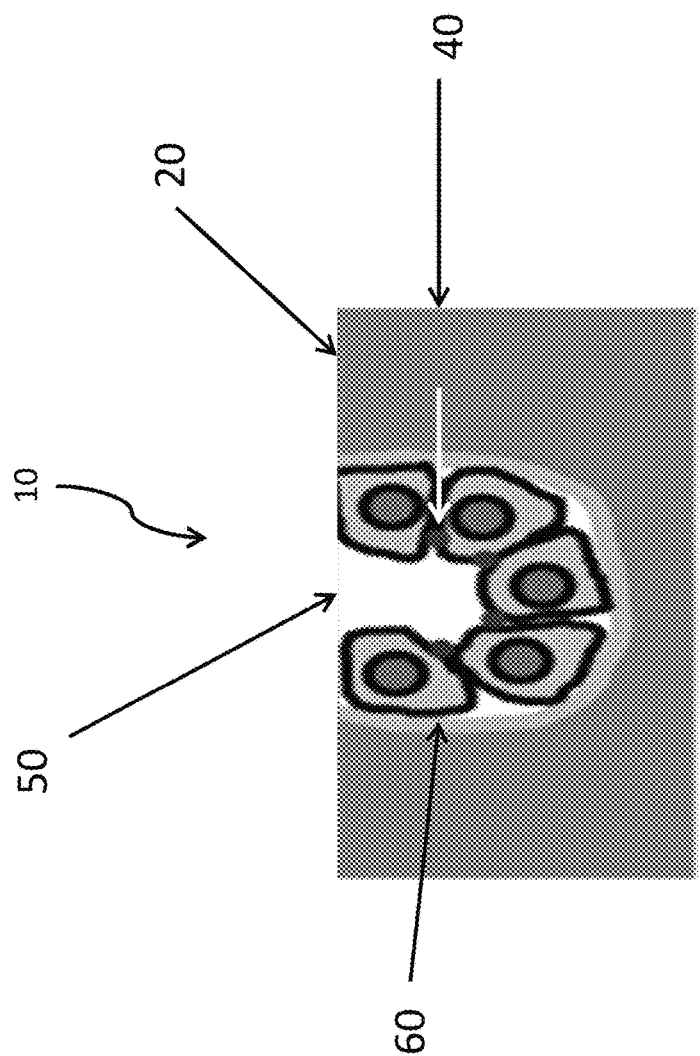
FIG. 24 is a cut away view of cartoon depiction of a general cell culture system, with a monolayer of polarized epithelial cells and a white arrow highlighting a tight junction.

The cell culture system and method may be used to test pharmaceutical drugs, repurposed drugs, or lead compounds prior to animal studies as shown in FIG. 23. Using the cell culture system, mammalian non-neoplastic, and mammalian neoplastic cells, tumors growing in lumens in an in vivo environment are mimicked and established. By "mammalian" refers to an animal of class Mammalia. Non limiting examples include humans, monkeys, dogs, cats, cows, and pigs. Compounds may be added to the medium by a carrier. The carrier may be water, saline, DMSO, cell culture medium, an alcohol, or a combination thereof. The response to the compounds may be analyzed over the term of the experiment to see if the tumors are inhibited, shrink, or ameliorated. This also allows for a visual of what happens to the non-neoplastic cells which are co-existing and/or supporting the tumors growth. The compounds are added in an amount between about 0.01 picograms and 10 micrograms/ semicircular hemichannel. The amount and concentration of a compound or combination of compounds will be dependent on several factors including the characteristics of the compound itself. Those of skill in the art will understand the need and procedure to develop $IC_{50}$ ranges for analysis. The system and method is also amenable to testing combinations of drugs to look for synergies. The compounds tested may be small molecules, biologics, hybrid molecules comprising both small molecule and biologics, macromolecules, antibody drug conjugates, hybrid molecules comprising both macromolecule and biologic, peptides, nucleic acids, natural products, synthetic products, products derived from nanotechnology, and combinations thereof. The system may be configured to work with a cell culture robot.

Figure 4:
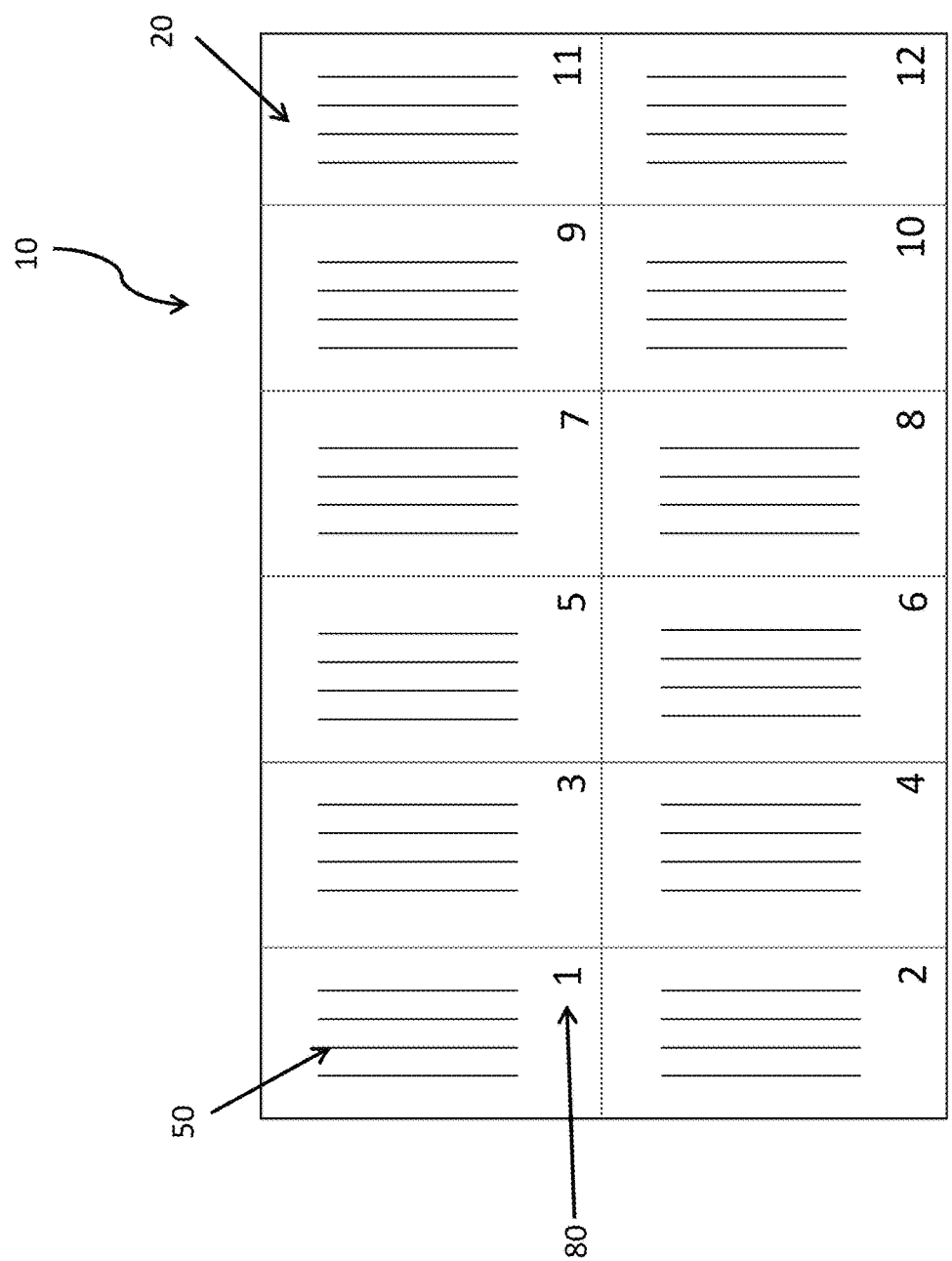
FIG. 4 is a cartoon showing a general scheme of a high throughput cell culture system where the separate domains are distinguished by a numbering system.

Testing a large numbers of compounds to generate a high throughput system may be ideal for drug discovery as shown in FIG. 23 and FIG. 28. The cell culture system and methods may be configured to operably couple with a cell culture robot. A high throughput system may be achieved several ways. In one embodiment, the cell culture system is generated on a planar member having separate domains. There may be up to 1,560 separate domains on a single planar member. The domains may be separated by spacers and the semicircular hemichannels may be organized differently in each domain. For instance, the semicircular hemichannels in each domain may traverse the domain in different directions along an axis compared to the other domains as shown in FIG. 3. In other aspects, the semicircular hemichannels may traverse the domain in the same direction in each domain as shown in FIG. 2. In this system, each domain may have the same epithelial monolayer of non-neoplastic cells, or each domain may have a monolayer of different types of epithelial non-neoplastic cells. Each domain may have the same neoplastic cells forming a tumor, or each domain may have a different seeding of neoplastic cells different from the other domains. Each domain may be testing the same compound, or each domain may be testing a different compound. The system may be designed so that each domain is identified by a distinct arrangement of a plurality of semicircular hemichannels, or they may be identified by a code or number system (80) as shown in FIG. 4. To introduce replicates into the high throughput system, several groupings of domains may be set up to have the same conditions, and the other groupings of domains may have different conditions. In other embodiments, each domain may have at least one different variable, and the replicates are generated by repeating this set up on a plurality of cell culture systems.

Another high throughput embodiment may be to generate separate cell culture system having a planar member having at least one semicircular hemichannel, wherein the cell culture system fits or inserts into a well of a multiwell plate as shown in FIG. 5. In this embodiment the size of the planar member and the number of semicircular hemichannels is dependent on the well size of the multiwell plate. Multiwell plates are commercially available currently having between 6 and 1,536 wells. As an exemplary embodiment, if a 96 well plate is chosen, the planar member may be a circle with a diameter of about 7,000 microns. The width of each semicircular hemichannel is dependent on the application but may range between 50 and 500 microns. In some instances, the width is between about 70 and about 120 microns. If the width is about 100 microns, then the planar member may comprise up to 70 separate semicircular hemichannels. The semicircular hemichannels may reach the edge of the planar substrate, or they may not which generates a border. If the semicircular hemichannels do not traverse to the edge of the planar member, there is a boarder of flat planar member around the semicircular hemichannels of at most about 20 microns.

In another embodiment of a specific example of a high throughput system (120) which comprises a holder device, a cell culture system, and a housing. Where the holder device comprises a fastener plate (110) and a carrier plate (100). Referring now to FIGS. 6,7,8,9,10, 11, 12 and 13, one component of this high throughput system (120) includes a holder device for securing the cell culture system (10) when it is inserted into a housing (90), such as a multiwell plate or a structure like a well plate. In one embodiment a system is described for holding a disease-on-a-chip system (10) in a housing (90), comprising a carrier plate (100), a disease-on-a-chip system (10), a fastener plate (110), and a housing (90). In one aspect the housing may be a multiwall plate comprise between 6 and 1,536 wells. In another aspect the carrier plate and fastener plate are made of plastic. In another aspect the disease-on-a-chip system is placed inside the carrier plate, and wherein the carrier plate can be removed from the well plate for analyses. This specific high throughput system is configured to be optically transparent from either the top of the system, the bottom of the system, or both.

The cell culture system and methods of use have broader application beyond research and drug discovery. The cell culture system and method may be used to grow a patient's own cells including non-neoplastic and neoplastic to investigate treatment options as well as another source for diagnosis. In one aspect, a patient diagnosed with a cancer will have a biopsy procedure performed. Part of the biopsy may be used to start a disease-on-a-chip system also referred to as a cell culture system. The established system may be used to test drugs on a tumor prior to prescribing the drugs to the patient to understand the medications possible effectiveness. In another embodiment, the neoplastic cells do not come from the patient, but from a different source such as a known cell line.

The following are examples demonstrating the cell culture system and methods.

Figure 14:
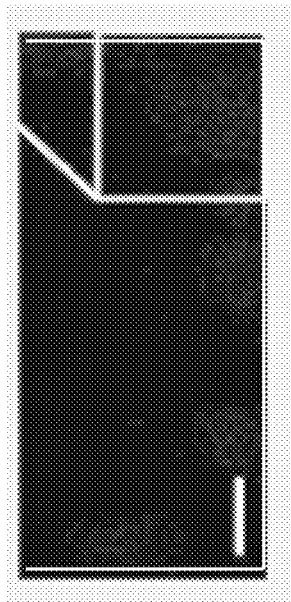
FIG. 14A and FIG. 14B show images of cells growing on a hemichannel in the shape of a rectangle, where in FIG. 14A shows clumping of cells in corners of the hemichannel.
Figure 14B:
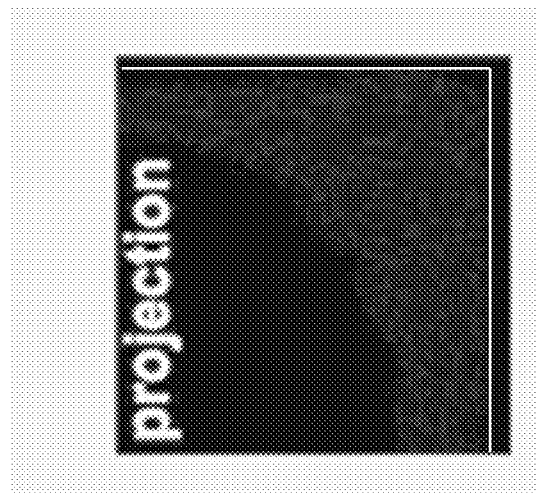

PDMS surfaces are compatible with cell growth, yet may cause artifacts. The effect on cell behavior of uncrosslinked polymers leaching from PDMS structures is unknown and adsorption of hydrophobic molecules—including steroid hormones—on PDMS surfaces is a matter of concern, especially for the culture of mammary epithelial cells. For models of the breast ductal system, another limitation is that PDMS hemichannels produced by conventional microfabrication techniques have a rectangular cross-section. Non-neoplastic mammary epithelial HMT-3522 S1 cells cultured on laminin-coated PDMS are organized into a polarized layer with apical tight junctions like in the luminal (outer) portion of the breast epithelium; however, they usually form multilayers in the corners of the channels when using rectangular hemichannels as shown in FIG. 14A and FIG. 14B. This issue had to be resolved because cell multilayering is one of the characteristics of solid tumor development.

A laser micromachining process was employed to produce acrylic-based hemichannels with a circular cross section. Semicircular hemichannels were engraved on SHAPE PRODUCTS acrylic sheets using a $CO_2$ laser cutting and engraving system operating in continuous wave mode at about 30 watts power and about 1 mm/ms. Focusing the laser on an acrylic surface yielded V-shaped cross-sections. To achieve semicircular cross-sections, the laser was focused about 0.5 to about 1 mm above the acrylic surface (depending on the desired diameter). Rough surfaces obtained after laser micromachining promoted cell growth as multilayers rather than the desired monolayer coating of the semicircular hemichannel walls usually found in vivo as shown in FIG. 15A and FIG. 15B. This issue was solved by smoothing the surfaces by spin coating polymethyl methacrilate (PMMA) at about 2000 rpm for about 30 sec; as shown in FIG. 16A and FIG. 16B. Treating the planar member having semicircular hemichannels with air plasma increased hydrophilicity, as observed from water contact angle measurements, which facilitated coating with laminin 111.

On laminin 111-coated PDMS surfaces, S1 epithelial cells in acrylic hemichannels were basoapically polarized with basal distribution of the polarity marker a6-integrin and the apical localization of the tight-junction marker ZO-1 as shown in FIG. 17A-FIG. 17C and FIG. 24.

Figure 18A:
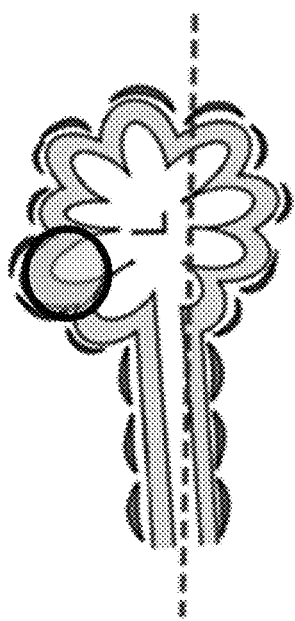
FIG. 18A and FIG. 18B are images of a tumor growing in vivo in a terminal duct lobular unit (TDLU), with FIG. 18A showing a cartoon representation of the a TDLU, with the acinus marked by a dark black circle, and FIG. 18B showing a hematoxylin-eosin staining of a histological section through a breast TDLU.
Figure 18B:
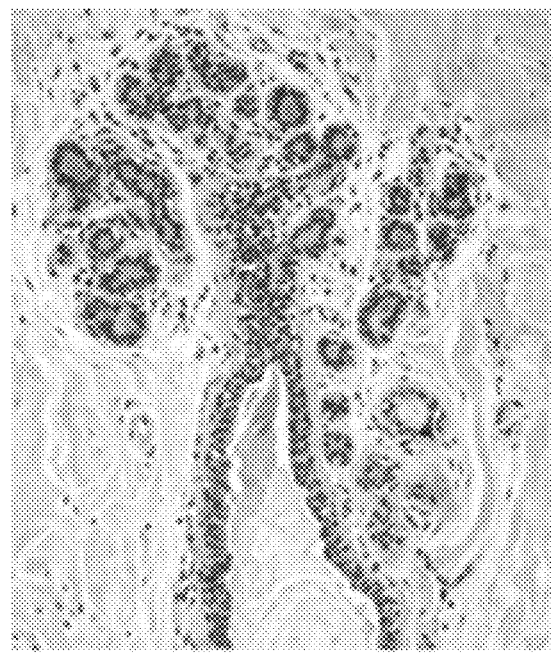

In solid cancers, tumors develop within the normal cell bed. In the breast, the cell bed encompasses the epithelium that delineates the ducts, and tumors initially develop via the accumulation of cells within the lumen of a ductal channel. It has been reported that the presence of non-neoplastic cells prevents the proliferation of tumor cells in culture. In these previous reports, the non-neoplastic cells were not mimicking the luminal epithelial architecture. Therefore, it was assessed in a first approach whether cancer cells could form tumors in the presence of predifferentiated acini using classical embedded three-dimensional (3D) cell culture. Normal acini are basoapically polarized, spherical structures made of myoepithelial cells surrounding the inner luminal epithelium organized into one layer around a central lumen. Groups of connected acini form the terminal ductal lobular units (TDLUs) prolonging mammary ducts as shown in FIG. 18A and FIG. 18B. S1 cells were induced to differentiate into the luminal portion of acinar structures for 10 days in the presence of MATRIGEL, then released from MATRIGEL with dispase, washed in medium, and mixed in MATRIGEL with small nodules containing a few S1-derived HMT3522 T4-2 cancer cells. The T4-2 nodules grew in coculture and, surprisingly, T4-2 cancer cells were attracted to acini and came in contact with acinar cells. Once in contact, they engulfed the acini completely, suggesting that, in an appropriate 3D microenvironment, small tumors strive in the presence of phenotypically normal epithelium. This behavior reflects the capacity of invasive cancer cells to colonize normal territories. However, this 3D MATRIGEL coculture system does not represent the in vivo tissue context in which a tumor develops within the lumen of the terminal ducts.

Therefore a cell culture system comprising acrylic semicircular hemichannels as described above was used to recapitulate the physiological context of mammary tumor development. First, the optimal coculture conditions for this system were determined. T4-2 cells seeded as small nodules (3-5 cells) on the S1 cell monolayer developed tumors (16,731±1,522 µm2; n=65), hence confirming that small tumor nodules thrive in the presence of the non-neoplastic cells. With this approach, more than 80% of T4-2 colonies exhibited 3D growth patterns after four days in coculture. Tumor nodules cocultured with S1 cells within the hemichannels were fixed with 4% paraformaldehyde and immunostained for CD44, a cell surface marker of cancer stem cells abundantly present in the T4-2 cell population. Confocal microscopy imaging revealed tumor nodules developing at the bottom or to the side of the hemichannels as shown in FIG. 19A-19C. The same observation was made when staining cell membranes of tumor nodules with DiI. This tumor pattern mimics the organization observed on sections of biopsies of cancerous tissue, with cancer cells infiltrating the epithelium, thereby contacting the basement membrane.

Figure 20B:
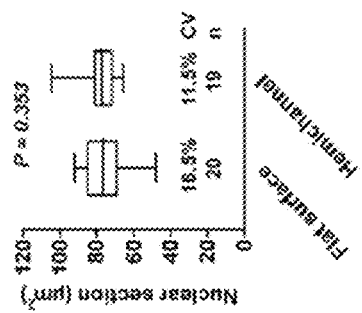
FIG. 20A-FIG. 20D show graphs comparing data of non-neoplastic cells growing on a flat surface versus in a semicircular hemichannel cell culture system, with FIG. 20A showing the difference in cellular section between flat and hemichannel, FIG. 20B showing the difference between nuclear section between flat and hemichannel, FIG. 20C showing the difference between cellular circularity between flat and hemichannel cultures, and FIG. 20D showing the measured difference between nuclear circularity between flat and hemichannel cultures.
Figure 20D:
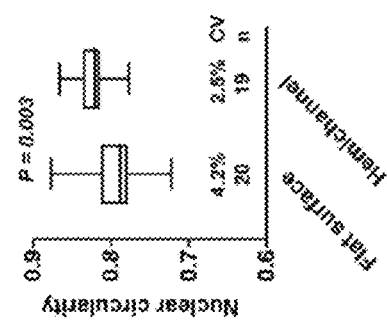
Figure 20A:
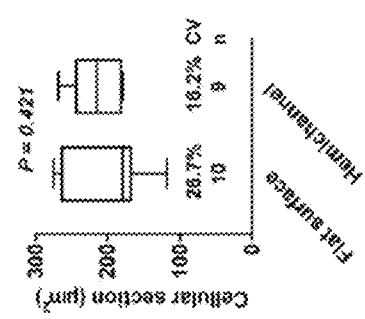
Figure 20C:
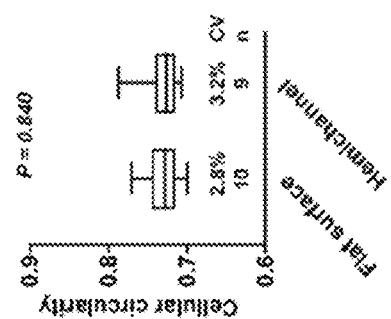

To further characterize the cell culture system co-culturing non-neoplastic and neoplastic cells, tumor nodules developing within hemichannels were compared to nodules on the flat surfaces, both lined with a monolayer of luminal epithelium. Morphological features of cancer cells are routinely analyzed in the clinic as part of the pathological evaluation of tumors. Hence, we measured the size and shape of the T4-2 cells and their nuclei. β-catenin immunostaining of the plasma membranes was used to delineate cell boundaries whereas nuclear morphological features were extracted from the DAPI images. Averaged cellular size and shape parameters were not different between nodules developing within the hemichannels vs. neighboring nodules on a flat surface. The average cross section (area) of nuclei was also comparable in both conditions as shown in FIG. 20A-20C. In contrast, the circularity of T4-2 nuclei differed depending on the location of the nodules. Nodules on flat surfaces had significantly less round nuclei compared to nodules in the hemichannels as shown in FIG. 20D. Also, nodules on flat surfaces displayed significantly higher variability for this shape parameter—both among nodules and within nodules. Similar observations were made for other nuclear shape descriptors including aspect ratio and solidity (i.e., area/convex area). Aggressive tumors are characterized by highly heterogeneous cellular features. In particular, nuclear pleomorphism (i.e., marked variations in nuclear sizes and shapes within tumors), is typically associated with high-grade breast cancers characterized by poorer prognosis.

Figure 21:
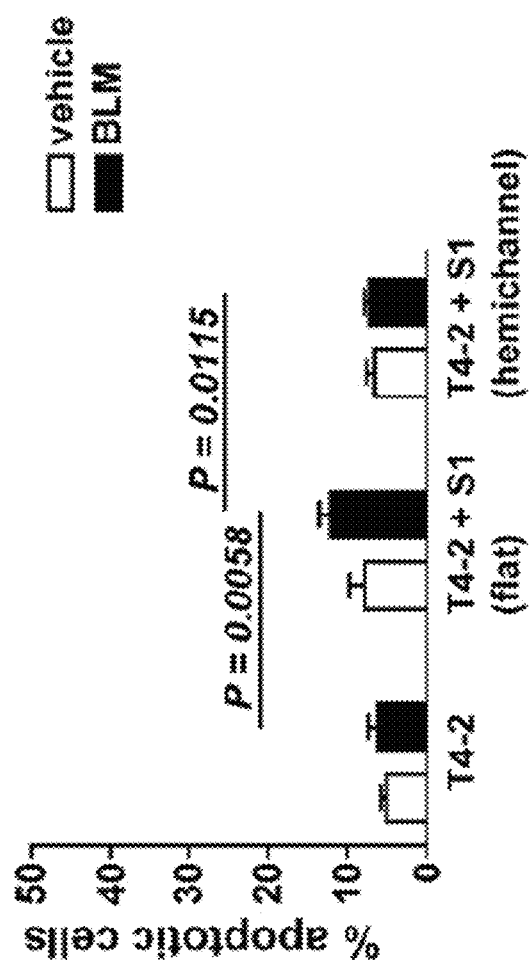
FIG. 21 is a graph showing the response to a chemotherapeutic drug called bleomycin (BLM) or vehicle, comparing the responses by measuring percentage of apoptosis of neoplastic cells (T4-2) grown alone on a flat surface, T4-2 cells co-cultured with non-neoplastic cells (S1) grown on a flat surface, and T4-2 co-cultured with S1 in a semicircular hemichannel when exposed to BLM or vehicle.
Figure 22:
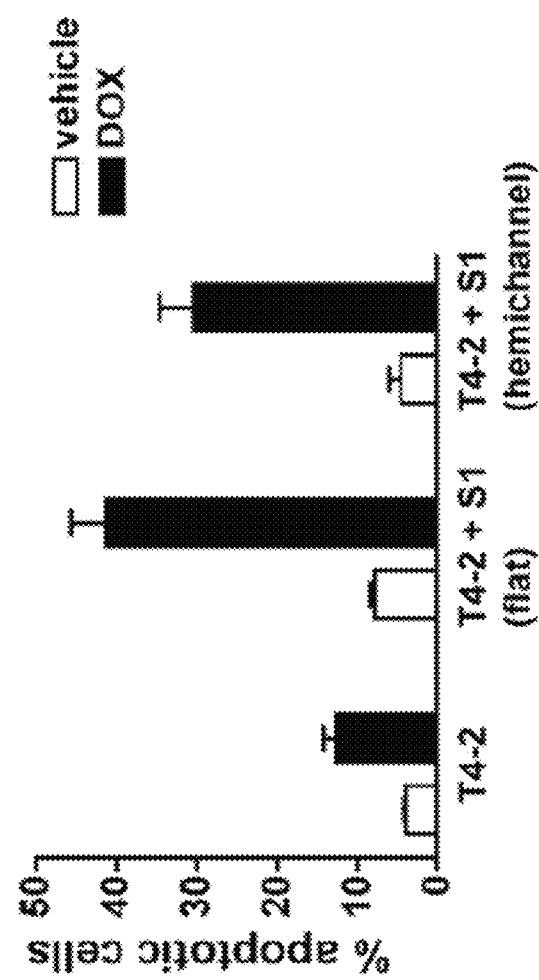
FIG. 22 is a graph showing the response to a chemotherapeutic drug called doxorubicin (DOX) or vehicle, comparing the responses by measuring percentage of apoptosis of neoplastic cells (T4-2) grown alone on a flat surface, T4-2 cells co-cultured with non-neoplastic cells (S1) grown on a flat surface, and T4-2 co-cultured with S1 in a semicircular hemichannel when exposed to DOX or vehicle.

The findings described above prompted a test of the sensitivity of T4-2 tumor nodules to the chemotherapeutic drugs bleomycin (BLM, a radiomimetic agent used in the laboratory to study cellular responses to treatments that compromise genome integrity) and doxorubicin (DOX, an anthracycline used for the treatment of breast cancer). In this study, apoptosis was utilized as an endpoint to evaluate drug responses and was quantified using the TUNEL assay combined with visual scoring for pyknotic and karyorrhectic nuclei via DAPI staining (i.e. nuclear condensation and fragmentation, respectively). Three types of T4-2 nodules were compared: monocultures, cocultures with S1 luminal epithelium on the flat surface of the chip, and cocultures with S1 epithelium in the semicircular hemichannels. The results revealed increased sensitivity to BLM and DOX of tumor nodules cocultured with the non-neoplastic breast epithelium on flat surfaces compared to monocultures of tumor nodules as shown in FIG. 21 and FIG. 22. The low toxicity of BLM to T4-2 nodules is expected since the drug concentration chosen is normally used to ease the detection of increased sensitivity to genotoxic stress and it should minimally affect cell survival.

Interestingly, sensitivity of cancer cells to DOX and BLM was significantly less for nodules that were located within semicircular hemichannels versus on flat surfaces as shown in FIG. 22. This difference is intriguing and could not be explained by the proliferation status within nodules on flat surfaces and in hemichannels (27.5%±1.8% and 24.2%±2.5% Ki67-positive cells, respectively; P=0.292, unpaired t-test, n>10 nodule sections corresponding to >700 nuclei). Moreover, similar effects were observed in cells treated with 3 Gy of ionizing radiations, suggesting that differences in apoptotic indexes did not merely result from altered drug penetration rates. It is possible that the microenvironment or the geometry in the hemichannels promotes modifications in the nuclear organization of tumor cells, which may influence cellular responses to cytotoxic drugs. This view is supported by the measured differences in nuclear circularity reported above, and is in agreement with early recommendations that nuclear morphometric descriptors, including roundness, should be investigated as possible predictors of response to therapy. The disease-on-a-chip system used for coculture with cancer cells provides a system with potential for improved understanding of cancer development and drug assessment in tissue context.

Figure 25:
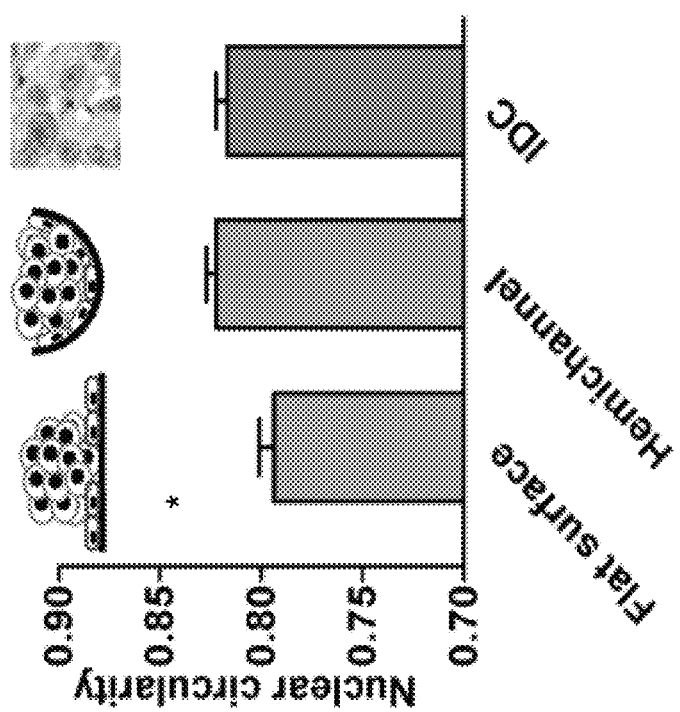
FIG. 25 is a graph comparing the nuclear circularity of a co-culture of neoplastic cell and non-neoplastic cells on a flat surface, a co-culture of neoplastic and non-neoplastic cells in a smooth semicircular hemichannel, and a stained section from a human breast carcinoma.
Figure 26B:
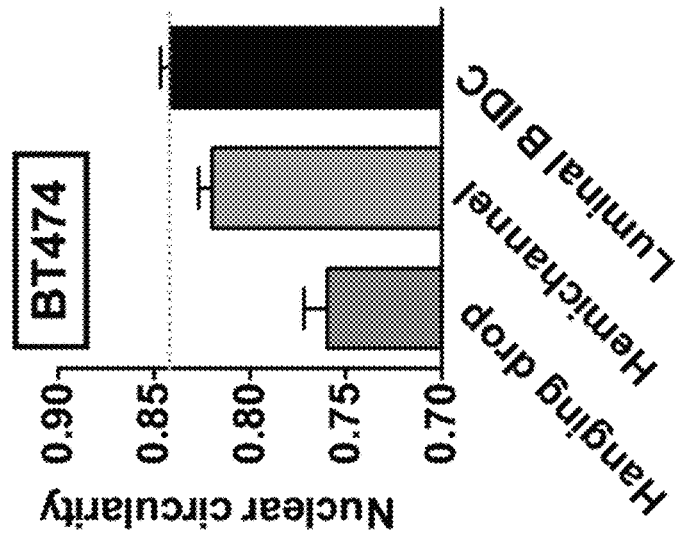
FIG. 26A and FIG. 26B are graphs comparing nuclear circularity, with FIG. 26A comparing the nuclear circularity of T4-2 breast cancer nodules cultured in a hanging drop, on a flat surface, in a semicircular hemichannel, and an ex vivo stained tissue section of the same type of cancer (triple negative invasive ductal carcinoma) as the one mimicked by T4-2 cells, and FIG. 26B comparing nuclear circularity of BT474 breast cancer nodules cultured in a hanging drop, on a flat surface, in a semicircular hemichannel, and an ex vivo stained tissue section of the same type of cancer (luminal B invasive ductal carcinoma) as the one mimicked by BT474 cells.
Figure 26A:
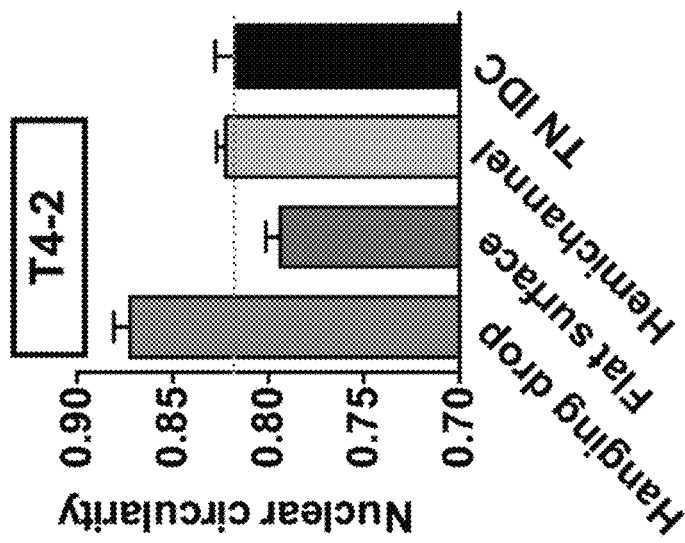
Figure 27:
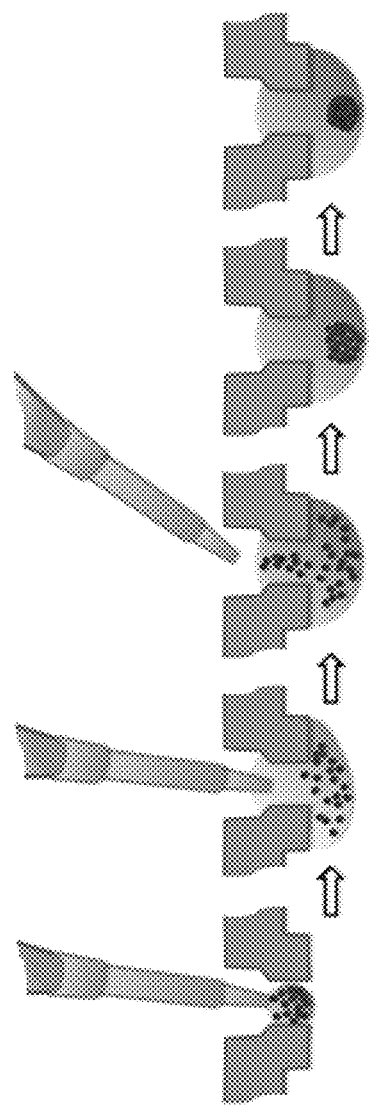
FIG. 27 is a cartoon depiction of how a tumor forms in a hanging drop.

Referring now to FIG. 25, FIGS. 26A, and 26B, it was observed that the nuclear circularity of two cancer types T4-2 and BT474 were similar when comparing neoplastic cells co-cultured in the cell culture system and in vivo tissue sections versus a flat surface co-culture or a hanging drop which are the currently used cell culture systems in research and drug discovery. For a cartoon depiction of a hanging drop, please refer to FIG. 27.

Those skilled in the art will recognize that numerous modifications can be made to the specific implementations described above. The implementations should not be limited to the particular limitations described. Other implementations may be possible.

References and citations to other documents, such as patents, patent applications, patent publications, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A cell culture system comprising at least one monolayer of non-neoplastic cells supporting tumor nodules, wherein both the non-neoplastic cells and the tumor nodules mimic in vivo phenotype, comprising;
   a planar member having at least one axis and thickness including at least one semicircular hemichannel extending in the direction of the at least one axis, the at least one semicircular hemichannel partially formed into the thickness of the member; and
   a polymer layer in direct contact with the semicircular hemichannel to provide a substantially smooth surface, wherein the substantially smooth surface is configured to receive a plurality of cells.

2. The cell culture system of claim 1, wherein the planar member comprises, acrylic, glass, plastic, or a combination thereof.

3. The cell culture system of claim 1, wherein the plurality of cells are non-neoplastic cells.

4. The cell culture system of claim 1, wherein the plurality of cells are non-neoplastic and neoplastic.

5. The system of claim 2, wherein the non-neoplastic cells are arranged in a monolayer.

6. The cell culture system of claim 1, wherein the polymer layer includes a cell attachment factor.

7. The cell culture system of claim 6, wherein the cell attachment factor is laminin 111.

8. The cell culture system of claim 1, wherein the at least one semicircular hemichannel has a width of between about 75 microns to about 120 microns.

9. The cell culture system of claim 1, wherein the planar member further comprises domains.

10. The cell culture system of claim 9, wherein the domains are separated by spacers.

11. The cell culture system of claim 10, wherein the spacer comprises acrylic, glass, plastic, PDMS, or a combination thereof.

12. The cell culture system of claim 9, wherein the planar member comprises up to 96 separate domains.

13. The cell culture system of claim 1, wherein the length of the planar member is about 127 millimeters to about 128 millimeters.

14. The cell culture system of claim 1, wherein the width of the planar member is about 85 millimeters to about 86 millimeters.

15. The cell culture system of claim 1, wherein the at least one semicircular hemichannel does not traverse to the edge of the planar member.

16. The cell culture system of claim 1, wherein the system is configured to interact with a cell culture robot.

17. A cell culture system comprising:
 a planar acrylic member having at least one axis and thickness including at least one semicircular hemichannel extending in the direction of the at least one axis, wherein the planar acrylic member is configured to insert into a well plate, the at least one semicircular hemichannel partially formed into the thickness of the member; and
 a polymer layer in direct contact with the semicircular hemichannel to provide a substantially smooth surface, wherein the substantially smooth surface is configured to receive a plurality of cells.

18. The cell culture system of claim 17, wherein the planar acrylic member is up to 7000 microns in length.

19. The cell culture system of claim 17, wherein the planar acrylic member includes up to 70 semicircular hemichannels.

20. The cell culture system of claim 17 wherein the cell culture system is configured to interact with a cell culture robot.

* * * * *